United States Patent [19]

Astrup

[11] Patent Number: 5,422,352
[45] Date of Patent: Jun. 6, 1995

[54] SLIMMING PHARMACEUTICAL COMPOSITION

[75] Inventor: Arne Astrup, Charlottenlund, Denmark

[73] Assignee: Nycomed Dak A/S, Copenhagen S, Denmark

[21] Appl. No.: 996,840

[22] Filed: Dec. 21, 1992

Related U.S. Application Data

[63] Continuation of Ser. No. 474,013, Jul. 2, 1990, abandoned.

[30] Foreign Application Priority Data

Jul. 7, 1989 [DK] Denmark ............................ 3392/89

[51] Int. Cl.$^6$ .................... A61K 31/52; A61K 31/135
[52] U.S. Cl. ...................................... 514/264; 514/653
[58] Field of Search ................................ 514/264, 653

[56] References Cited

U.S. PATENT DOCUMENTS 4,364,922 12/1982 Berne et al. ............................ 424/9
5,011,843 4/1991 Shell ...................................... 514/259

FOREIGN PATENT DOCUMENTS 0120165 10/1984 European Pat. Off. .
2390164 5/1977 France .
2004183 3/1982 United Kingdom .

OTHER PUBLICATIONS

Anderson et al (1987), Federation Proceedings 1021.
Warris et al (1990), J. Anim. Sci. 68, 128–136.
Veenhuizen et al (1987), J. Anim. Sci. 65, 130.
Peterla et al (1987), J. Anim. Sci. 65, 278.
Peterla et al (1988), J. Anim. Sci. 66, 249.
Thornton et al (1985), Proc. New Zealand Soc. Anim. Prod. 45, 97–101.
Adeola et al (1989), J. Anim. Sci. 67, Suppl. 1, 191.
Wilson et al (1988), Nutrition Research 8, 1287–1296.
EEC 1979, Document VI/5804/78 rev.
Unlisted Drugs, vol. 29, No. 1, 1980.
Dulloo et al (1985), Proc. Nutr. Soc. 44, 16A.
Wellman et al (1985), Pharmacol. Biochem. Behaviour 22, 781–785.
Council on Scientific Affairs, 1988, Jama 260, 2547–48.
Dulloo et al, 1989, Nutrition 5, 7–9.
Astrup, 1989, Nutrition 5, p. 70.
Astrup, 1986, Acta Endocrinol. 112, suppl. 278, 1–32.
Hollands et al, 1981, AmJ. Clin. Nutr. 34, 2291–2294.
Astrup et al, 1985, AmJ. Physiol. 248, E 507–514.
Astrup, 1987, J. Obes. Weight Reg. 6, 3–20.
Dulloo et al, 1986, Int.J.Obesity 10, 467–481.
Cesari et al, Int.J. Obesity 13, Suppl. 1, 152, 1980.
Editorial, 1984, Drug Treatment, Jul. 1984, 43–51.
Sebok, 1985, Curr.Ther. Res. 37, 701–708.
Goth, 1981, Medical Pharm. 10th Ed., Mosby Publ., U.S.A. p. 190ff.
Arch et al, 1984, Nature, 309, 163–165.
Durnin et al (1974) Br. J. Nutr. 32, 77–97.
Jequier (1987), Body Weight Control.
Segal (1987), Am. J. Clin. Nutr. 45, 1420–1423.
Scholander (1947), J. Biol. Chem. 167, 235.
Weir (1949), J. Physiol. 109, 1–9.
Garby et al. (1987), Acta Physiol. Scand. 129, 443–444.
Laurell et al. (1967), Clin. Chim. Acta, 16, 57–62.
Laurell et al. (1966), Clin. Chem. Acta 13, 317–322.
Giegel et al. (1975), Clin. Chem. 21, 1575–1581.
Christensen et al (1980), Acta Psychiat. Scand. 61, 178–182.

(List continued on next page.)

*Primary Examiner*—Raymond Henley, III
*Assistant Examiner*—P. Spivak
*Attorney, Agent, or Firm*—Birch, Stewart, Kolasch & Birch

[57] ABSTRACT

The present invention is directed to a method for reducing the weight of a human and a method for reducing the adipose tissue mass/lean mass body mass ratio of a human or a domestic animal. In each method, an effective dose of a combination of ephedrine and caffeine are administered in a weight ratio of about 1:12, respectively, calculated on the amount of ephedrine in the form of the free base.

14 Claims, 15 Drawing Sheets

OTHER PUBLICATIONS

Wellems et al (1985), Pharm. Weekbl. Sci. Ed. 7, 150.
Lurie (1981), J. Liq. Chromatogr. 4, 339.
Lai et al (1979), J. Pharm. Sci. 68, 1243.
Nelder et al (1965), Comput. J. 7, 308.
Anderson et al (1986), Nutrition 2, 83–86.
Quaade et al (1988), Medicographica 10, 21–23.
Kenward (1987), Appl. Statist. 36, 396–308.
Whitlemore et al (1988), Anim. Prod. 46, 437–445.
Donker et al (1986), Livest. Prod. Sci. 15, 353–365.
Oksbjerg et al, Acta Agric. Scand., 1980.
Warriss et al, J. Anim. Sci. 68, 128–136, 1979.
Jensen et al (1980), Ugeskr. Laeger, 1499–1501.
Williams (1987), Nutrition Abstracts and Reviews, 57, 453–464.
Tulp et al (1986), Comp. Biochem. Physiol. 85C, 17–19.
Dulloo et al (1987), J. Nutri. 117, 383–389.
Dulloo et al (1986), Am J. Clin. Nutr. 43, 388–394.
Miller (1986), Int. J. Obes. 10, 159–160.
Dulloo et al (1987), Wld. Rev. Nutr. Dict. 50, 1–56.
Dulloo et al (1984), Br. J. Nutr. 52, 179–196.
Dulloo et al (1989), Am. J. Clin. Nutr. 49, 44–50.
Jung et al (1981), Clin. Sci. 60, 527–535.
Toubro et al (1986), Acta Physiol. Scand. 128, 33A.
Lee et al (1987), Am. J. Physiol. 21, R737–$742.
Dulloo et al (1986), 1–Pharmacology, vol. 106, 1987.
Chem. Abst. 107–1763R (1987).
Chem. Abstracts 106 (5): 27678w Tulp et al.
Chem. Abstracts 101 (17): 144000b Dulloo et al.
Chem. Abstracts 97 (23): 193080k Wilcox.
Martindale, The Extra Pharmacopeia, 28th edition (1982) pp. 11, 12, 340, 341.
Modern Pharmacology, Craig et al. (1982) pp. 138 & 139.
Goodman et al. The Pharmacological basis of Therapeutics, 6th edition (1980) pp. 163, 164 and 592–607.

SLIMMING PHARMACEUTICAL COMPOSITION

This application is a continuation of application Ser. No. 07/474,013 filed on Jul. 2, 1990, now abandoned.

FIELD OF INVENTION

The present invention relates to a pharmaceutical composition comprising a directly or indirectly acting $\beta$-adrenerg agonist, e.g. ephedrine, and a xanthine, e.g. caffeine, to the use thereof for the treatment of overweight or obesity, or complications to overweight or obesity, and to the use thereof in domestic animals for an improvement of the body content of meat at the expense of the body content of fat.

GENERAL BACKGROUND

Overweight and obesity

Obesity is a disease especially widespread in prosperous, industrialized countries. Obesity can be defined as an excessive accumulation of fat in the body. Such excessive accumulation of fat can take place as a consequence of an energy intake which is greater than the energy expenditure, arising from either an excess of energy intake (i.e. a surplus of food) or a reduced energy expenditure.

For practical purposes, it is generally agreed that overweight is present if the body weight exceeds the "desirable weight", whereas obesity is present if the body weight is 20% or more above the "desirable weight" (1). Desirable weights for humans can be defined according to Metropolitan Height and Weight Tables (1) as the midpoint of the range of the medium-frame individuals.

Obesity can be classified as a mild (20-30% overweight), moderate (30-60% overweight) or a severe ($\geq$60% overweight) condition. Obesity is accompanied by a number of health hazards. It may impair both cardiac and pulmonary functions, perturb endocrine functions and cause emotional problems. Hypertension, impaired glucose tolerance and non-insulin dependant diabetes mellitus and hypercholesterolemia are more common conditions in overweight individuals than in individuals of normal weight. Obesity may therefore contribute to morbidity and mortality in individuals suffering from e.g. hypertension, stroke, diabetes mellitus type II, some types of cancer, gallbladder disease and ischaemic heart disease. Moderate and severe cases of obesity are known to increase mortality. Colonic and rectal cancer are diseases which frequently appear in obese men, and obese women often suffer from endometrium or gallbladder cancer. Furthermore, it is realized that an increase in overweight almost consequently leads to a rise in psychic and social problems.

Methods of treatment

The causes of obesity are complex and not fully understood. Obesity can be a result of life-style, i.e. of patterns of physical activity and food consumption, or a result of genetic propensity of the obese person. Genetic influences are generally considered to have an important role in determining human fatness and obesity. Furthermore, adverse reactions in the form of development of obesity can be seen after therapeutic treatment with various drugs.

The basic principle of treatment of obesity or overweight is to establish a negative energy balance. A negative energy balance can be accomplished using mainly three different methods of treatment or combinations thereof.

Firstly, an effective treatment is the reduction of energy intake, i.e. food intake. This is essentially possible only through a dietary treatment as malabsorption of food cannot be obtained safely either through medication or surgery. The dietary treatment must consist of a weight reducing diet as well as a maintaining diet. After a satisfactory weight loss, the energy supply must slowly be increased until the weight has stabilized on a supply of food which is nutrious and acceptable for the patient. The importance of a long-term diet is seen from the fact that only 10-20% of the patients are able to maintain their obtained reduced weight.

Secondly, increase in physical activity will lead to increased energy expenditure and consequently contribute to a negative energy balance. However, in order to obtain a significant weight loss, hours of daily physical activity is needed. Physical activity alone therefore plays a minor role in the treatment of obesity, although it is a very important supplement to other kinds of treatment. Also, physical activity can contribute to diminution of the decrease in energy expenditure which follows a dietary treatment comprising an energy restriction.

Thirdly, drugs can be used in the treatment of obesity, either alone or in combination with a dietary treatment and/or increased physical activity. The drugs used in the treatment of obesity can be appetite-reducing drugs and/or thermogenic drugs. Often, however, some overlap will be observed within the two categories. The appetite-reducing drugs exert their effect primarily by decreasing energy intake. The reduction in food consumption is a consequence of the drug action on the brain transmitter systems that are involved in the appetite regulation. The action of these drugs is supposed to be mediated through the hypothalamus at various sites. The action can be exerted through the adrenergic, the dopaminergic or the serotonergic pathway or a combination thereof. Whichever system is involved, the final result is a stimulation of the satiety center and eventually a simultaneous decrease in activity of the feeding center which results in a depressed appetite. Examples of known appetite-reducing agents are e.g. ephedrine, phenylpropanolamine, amphetamines and fenfluramine.

Thermogenic drugs in the treatment of obesity are now generally accepted to possess a potential therapeutic value, and in the recent years there has been a growing interest in the search for new thermogenic compounds. The interest is primarily related to the well accepted suggestion that obesity might be genetically determined. The genetic defect responsible for the possible development of obesity relates to a thermogenic defect (i.e. a defect in the metabolic system) of the obese person (2). Although the nature of the thermogenic defect is not fully clarified, there is a compelling evidence that points to a defective reactivity of the sympatoadrenal system (3). Dulloo & Miller (2) suggest that the thermogenic defect of the obese persons relates to a reduced release of norepinephrine rather than to an insensitivity to the neurotransmitter. Drugs which mimic the activity of the sympathetic nervous system and increase metabolic rate therefore offer considerable therapeutic potential for the treatment of obesity.

A thermogenic drug can be defined as a drug capable of raising metabolic rate, i.e. increasing the energy expenditure. Known thermogenic drugs are e.g. ephedrine, epinephrine, norepinephrine (4), isoproterenol, phenylpropanolamin and caffeine (5).

Studies concerning treatment of obesity in animals as well as in humans have been carried out with thermogenic drugs either alone or in combination. It has recently been shown that the major tissue of thermogenesis in rodents is the brown adipose tissue (BAT) (4). This is supported by the finding that resistance to obesity during voluntary overfeeding in rats and mice is due to an enhanced thermogenesis in BAT. It has been suggested that BAT is a determinant of energy expenditure in humans as well, and that defective thermogenesis in BAT contributes to human obesity. Human BAT receives sympathetic innervation, but the amounts of BAT are minute. It has been demonstrated that the thermogenic potential of human BAT is of minor importance compared to the total thermogenic response of the body (4). Resting skeletal muscle may contribute with at least 50% to the whole body thermogenesis induced by ephedrine (6), and skeletal muscle is probably a major determinant of resting metabolic rate as well as of the thermic effect of food in man (7). The major determinant of thermogenesis is thus quite different in man and rodents which makes a comparison between results from human and rodent studies meaningless. Thus, only results from human studies are reported in the following.

Dulloo & Miller (8) have recently shown that an over-the-counter tablet containing ephedrine and methylxanthines (22 mg ephedrine, 30 mg caffeine and 50 mg theophylline) (Do-Do pill, Ciba Geigy, UK) was twice as effective as ephedrine alone in increasing the fasting metabolic rate of both obese and lean human volunteers. As outlined in a review by Dulloo & Miller (2), it seems that the influence of methylxanthines effect of ephedrine but no detailed study seems to have been carried out in humans.

Cesarii et al. (9) have reported a randomized double-blind 4 months study in obese women. The women received either ephedrine alone (50 mg), ephedrine plus caffeine (50 mg+100 mg) or placebo without active drug(s), respectively, the drugs being administered orally. The study showed no significant difference in weight loss in the three treatment groups, indicating no interaction between ephedrine and caffeine.

The "Elsinore tablet" (10) consisting of ephedrine 20 mg, caffeine 55 mg and bisacodyl 1 mg was initially used against asthma but was observed to cause weight loss. This composition has been compared with ephedrine 20 mg (2+2+1 tablet per day) in a double-blind clinical trial on 64 obese patients (41). After 18 weeks, the average weight loss was 7.9 kg and 9.4 kg after administration of the ephedrine tablets and the "Elsinore tablets", respectively. However, the difference was not statistically significant (P>0.10).

Oral compositions with a combination of phenylpropanolamine hydrochloride and caffeine have been described in literature (11). Caffeine has probably been added to these compositions in order to allay fatigue (12) as caffeine has stimulating properties.

Various other combinations of ephedrine or pseudoephedrine and methylxanthines have emerged as over-the-counter pharmaceutical compositions for treatment of bronchial cough, wheezing, breathlessness and to clear the chest. In accordance with these therapeutic indications for use of such combinations, the potential use of such over-the-counter products as thermogenic compositions have not been reported according to our knowledge, except in the case of the Do-Do pill as referred to above in the study of Dulloo & Miller (8).

Carcass quality in domestic animals

Improvement of carcass quality, i.e. decrease in the fat tissue mass/lean body mass ratio, in meat animals is a goal in livestock science, because excess fat production are sources of inefficiency in the livestock and meat processing industry. Furthermore, excessive intake of dietary lipid by humans has been linked to an increased occurrence of coronary heart diseases in the human population.

Carcass composition of meat animals can be changed by feeding strategy using entire males or by killing animals at lower proportion of mature weight and through selection programs.

In addition, anabolic steroids have been extensively used in cattle to stimulate body growth and protein deposition. However, the anabolic steroids have recently been banned in the EEC countries which has contributed to an increased attention to new classes of compounds, such as $\beta_2$-adrenergic agonists (clenbuterol, cimaterol, ractopramine and salbutamol (42–45)) and growth hormone.

SUMMARY OF THE INVENTION

The therapeutic need for compounds capable of influencing the energy balance within an organism by increasing the energy expenditure has been discussed above and examples of such thermogenic compounds have been given.

It has now surprisingly been found that administration of certain combinations of the thermogenic drugs ephedrine and caffeine not only results in a thermogenic effect related to the two active principles, but also results in a thermogenic effect which is much higher than expected based upon the individual thermogenic effect of the separate compounds. Thus, a highly beneficial therapeutic effect on various conditions caused by disorders in the energy balance system (e.g. obesity) or by complications to overweight or obesity can be achieved using a suitable combination of a adrenerg agonist and a xanthine. Furthermore, an improvement of the carcass quality of domestic animals can be achieved due to the effect of the combination of the two active principles.

The present invention is based on the above-mentioned discovery and, in one aspect, it relates to a pharmaceutical composition comprising, as the essential active principle, a combination of ephedrine or another directly or indirectly acting thermogenically active and/or appetite-reducing adrenerg agonist, such as a $\beta$ agonist (e.g. $\beta_1$, $\beta_2$ and/or $\beta_3$ agonist) and caffeine or another thermogenically active xanthine in a weight ratio from about 1:8 to about 1:24, calculated (when the $\beta$ agonist is not L-ephedrine) on the isothermogenic amount of L-ephedrine and (when the xanthine is not caffeine) on the isothermogenic amount of caffeine.

In contrast to the traditional treatment of overweight or obesity or excellent clinical results have been obtained according to the present invention by using a pharmaceutical tablet composition comprising the above-defined combination of ephedrine and caffeine in patients suffering from overweight or obesity. The results from the clinical studies have clearly demonstrated that the action exerted by the combination of ephedrine and caffeine is due to an unexpected synergistic effect of the two drugs.

In another aspect, the invention relates to a method of treating overweight or obesity, either by reducing weight or by reducing adipose tissue mass/lean body mass ratio of an animal except a rodent, the method comprising administering to the animal a thermogenically effective dose of ephedrine or another directly or indirectly acting thermogenically active and/or appetite-reducing adrenerg agonist, such as a $\beta$ agonist (e.g. $\beta_1$, $\beta_2$ and/or $\beta_3$ agonist) and caffeine or another thermogenically active xanthine in a weight ratio from about 1:8 to about 1:24, calculated (when the $\beta$ agonist is not L-ephedrine) on the isothermogenic amount of L-ephedrine and (when the xanthine is not caffeine) on the isothermogenic amount of caffeine, said dose administered either as a single dose comprising a combination of the two active drugs or as separate doses administered substantially concomitantly and each dose containing one of the active drugs, respectively.

In a still further aspect, the present invention relates to a method of treating complications to overweight or obesity such complications as diabetes mellitus type II, hypercholesterolemia, hypertriglyceridaemia and hypertension, the method comprising administering to the animal a thermogenically effective dose of a directly or indirectly acting thermogenically active and/or appetite-reducing adrenerg agonist and a thermogenically active xanthine in a weight ratio from about 1:8 to about 1:24, calculated (when the $\beta$ agonist is not L-ephedrine) on the isothermogenic amount of L-ephedrine and (when the xanthine is not caffeine) on the isothermogenic amount of caffeine, said dose administered either as a single dose comprising a combination of the two active drugs or as separate doses administered substantially concomitantly and each dose containing one of the active drugs, respectively.

Preferably, the administration of the combination of an adrenerg agonist and a xanthine is accompanied by subjecting the individuals to a dietary regimen.

The present invention also relates to the use of a combination of an adrenerg agonist and a xanthine in a weight ratio from about 1:8 to about 1:24, calculated (when the $\beta$ agonist is not L-ephedrine) on the isothermogenic amount of L-ephedrine and (when the xanthine is not caffeine) on the isothermogenic amount of caffeine for the manufacture of a pharmaceutical composition for the treatment of overweight or obesity or of diseases aggravated thereof. The pharmaceutical composition comprising either one dosage form with simultaneous content of the two drugs or the dosage forms enclosed in two distinct containers, each containing the dosage form of one of the active drugs, respectively, and with enclosed instructions for substantially concomitantly use of the two drugs.

Furthermore, the present invention relates to a method for reducing fat tissue mass/lean body mass ratio of a domestic animal, the method comprising administering to the animal an effective dose of a combination of a $\beta$ adrenerg agonist (e.g. ephedrine) and a xanthine (e.g. caffeine).

The present invention also relates to the use of a combination of a $\beta$ adrenerg agonist (such as ephedrine) and a xanthine (such as caffeine) for the manufacture of a composition for improvement of carcass quality of a domestic animal by a reduction of the fat tissue mass/lean mass body mass.

DETAILED DISCLOSURE OF THE INVENTION

Drugs that act directly on adrenergic receptors, or release mediators which then act on the receptors, are generally termed sympatomimetics or adrenergic drugs. The sympatomimetics may be classified according to their mode of action into three categories: those having a direct effect, those exerting an indirect action through endogenous catecholamine release, and those having mixed effects, i.e. acting by both mechanisms (13). In the present context the term "directly or indirectly acting adrenerg agonist" denotes a substance acting as a sympatomimetic either by exerting the effect by a direct, indirect or a mixed mode of action.

The classification of adrenergic receptors as $\alpha$ and $\beta$ is now generally accepted. The concept was based on the order of activity of a series of sympathomimetic drugs at various effector sites and was greatly strengthened when specific blocking agents were developed for each receptor. The functions associated with $\alpha$ receptors are mainly vasoconstriction and mydriasis. $\beta$ Receptors mediate adrenergic influences for e.g. vasodilatation, cardioacceleration, bronchial relaxation, intestinal relaxation and metabolic effects as increased lipolysis, gluconeogenesis etc. Two main types of $\beta$ receptors is known, i.e. $\beta_1$ and $\beta_2$. The distribution of these types of receptors in various tissues is not sufficiently clarified at present. However, in general it is assumed that $\beta_1$ receptors are mainly present in the heart, whereas $\beta_2$ receptors dominate in the bronchi and in the smooth muscle tissues of the vascular system and of the liver and the pancreas. The $\beta$ receptors on the adipocytes are of a mixed population of $\beta_1$ and $\beta_2$ whereas skeletal muscle is substantially exclusively endowed with $\beta_2$ receptors. Recently it has been indicated that other types of $\beta$ receptors may exist. Thus, it has been found that the $\beta$ adrenoceptors in rat brown adipocytes are of neither the $\beta_1$ nor $\beta_2$ type (14).

In this context the term "a thermogenic compound" or "a thermogenically active compound" is understood to mean a compound which is within a living animal capable of raising metabolic rate, i.e. increasing energy expenditure.

Thermogenic compounds according to the invention are found in two different classes of therapeutically active substances, i.e. one class comprising $\beta$ adrenerg agonists and the other class comprising xanthines. The term "therapeutically active substance" as used herein is intended to mean any physiolocially or pharmacologically active substance that produce a localized or systemic effect in animals, except a rodent, in particular in mammals, including humans, primates and domestic animals.

Examples of directly or indirectly acting thermogenically active and/or appetite-reducing $\beta$ adrenerg agonists according to the present invention are ephedrine, salbutamol, terbutaline, clenbuterol, isoproterenol, metaraminol, etilefrin, norephedrine and pseudoephedrine, yohimbine, tyramine, amphetamine, cinnamedrin, hydroxyephedrine, methylephedrine, mephentermine, phenylephrine, nylidrin, isoxsuprine and diethylpropion or pharmaceutically acceptable salts or derivatives thereof. In one embodiment the use of ephedrine is preferred in form of L-ephedrine selected from the group consisting of (1R, 2S)-2- methyl-amino-1-phenyl-1-propanol, (1S, 2R)-2-methylamino-1-phenyl-1propanol and combinations thereof. The group also includes pharmaceutically acceptable salts and pro-drugs of the compounds.

The thermogenically active xanthine according to the present invention may be a methylxanthine, selected from the group of caffeine, theobromine, theophylline, aminophylline, acepifylline, etofylline, proxyphylline, diprophylline, choline, theophyllinate, enprofylline, bamiphylline, bufylline, etamiphylline, heptaminolacephyllinate, pimefylline nicotinate, protheobromine and suxamidofylline or pharmaceutically acceptable salts, complexes or derivatives thereof. Especially the use of caffeine is preferred.

Pharmaceutically acceptable salts of the thermogenic compounds according to the present invention include salts of strong inorganic acids or week organic acids, for example a hydrochloride, sulfate, nitrate and acetate salt.

In this context, the term "prodrug" denotes a bioreversible derivative of the drug, the bioreversible derivative characterized in being therapeutically inactive per se but being able to convert to the active drug within the organism either by an enzymatic or non-enzymatic process.

Examples of suitable prodrugs of the thermogenic compounds according to the present invention include compounds obtained by suitable bioreversible derivatization of one or more reactive groups of the parent drug.

Pharmaceutically acceptable complexes of the thermogenic compounds according to the invention include complexes like caffeine sodium benzoate.

The combination according to the present invention which comprises the two thermogenic compounds in a weight ratio from about 1:8 to about 1:24, preferably from about 1:8 to about 1:20, especially from about 1:8 to about 1:18, in particular from about 1:10 to about 1:16, such as about 1:12, calculated (when the $\beta$ agonist is not L-ephedrine) on the isothermogenic amount of L-ephedrine and (when the xanthine is not caffeine) on the isothermogenic amount of caffeine which ratio, after administration to an animal except a rodent, preferably a mammal, especially preferred a human, leads to a supra-additive thermogenic effect.

A supra-additive effect of a combination of two compounds can be recognized by measurements of the thermogenic effects after administration of the compounds separately and in combination, respectively, to human volunteers in a double-blind, placebo controlled clinical study. In the present context, the supra-additive thermogenic effect (SAE) is defined as the ratio between the actual thermogenic effect of the combination of the two drugs (AEC) and the predicted thermogenic effect of the combination (PEC). PEG can be calculated as the thermogenic effect of the $\beta$ adrenergic agonist (e.g. ephedrine) plus the thermogenic effect of the methylxanthine (e.g. caffeine), each thermogenic effect being determined separately, and the individual effects are each corrected for placebo effects. The actual value of supra-additive effect can be expressed in percentage by use of the following equation:

$$SAE\ (\%) = \frac{(AEC - PEC) \times 100\%}{|PEC|}$$

where $|PEC|$ in the denominator is the numerical value of PEC.

As a result of such a double-blind, placebo-controlled clinical study, the determined supra-additive thermogenic effect is normally at least about 10% higher, in particular at least about 30% higher, more preferably at least about 50% higher, most preferably at least about 70% higher than the sum of the thermogenic activities of the components administered separately as the sole medication, calculated as described above.

To achieve a therapeutically significant supra-additive thermogenic effect, the two drugs used in combination should be present in a weight ratio between the $\beta$ adrenergic agonist and the xanthine from about 1:8 to about 1:24, preferably from about 1:8 to about 1:20, especially from about 1:8 to about 1:18, in particular from about 1:10 to about 1:16, such as about 1:12, calculated (when the $\beta$ agonist is not L-ephedrine) on the isothermogenic amount of L-ephedrine and (when the xanthine is not caffeine) on the isothermogenic amount of caffeine.

In this context an isothermogenic amount of two or more compounds are the doses which after oral administration in fasted subjects increase the whole body energy expenditure to the same extent. The study should be performed in healthy volunteers and the increase in whole body energy expenditure can be calculated as the integrated part of the curve above baseline at a suitable time after administration, which curve can be obtained from a plot of the energy expenditure against time.

In a preferred embodiment of the invention the pharmaceutical composition comprising as the essential active principle a combination of ephedrine and caffeine in a weight ratio from about 1:8 to about 1:24, preferably from about 1:8 to about 1:20, especially from about 1:8 to about 1:18, in particular from about 1:10 to about 1:16, such as about 1:12.

The therapeutic dosage range for the compounds according to the present invention will vary with the size and need of the animal being treated and the particular disease or disease symptom. However, generally speaking the following guidelines will suffice. For oral administration, the amount of L-ephedrine or the other directly or indirectly acting thermogenically active and/or appetite-reducing adrenerg agonist, such as a $\beta$ agonist is about 10–40 mg per unit dose, in particular about 10–30 mg, such as about 16–17 mg per unit dose, calculated (when the $\beta$ agonist is not L-ephedrine) on the isothermogenic amount of L-ephedrine. The dose can be given from 1 to about 10 times daily, preferably from 2 to about 8 times daily, in particular from 2 to about 4 times daily. The dosage ranges given above are ranges based on L-ephedrine in the form of free base. Equivalent ranges for e.g. ephedrine hydrochloride can be calculated taking into account the difference in molecular weight of the ephedrine in the form of the free base and the ephedrine in the form of the hydrochloride. Thus, 1 mg of the ephedrine in the form of the free base corresponds to 1 mg×(MW of ephedrine hydrochloride/MW of ephedrine)=1 mg×1.20=1.20 mg.

For oral administration, the amount of caffeine or the other xanthine is about 80 mg-1.9 g per unit dose, in particular about 80 mg-720 mg, especially 80 mg-500 mg, such as 180–220 mg calculated (when the xanthine is not caffeine) on the isothermogenic amount of caffeine. The dose can be given from 1 to about 10 times daily, preferably from 2 to about 8 times daily, in particular from 2 to about 4 times daily.

The composition according to the present invention may be formulated for administration by any suitable route such as the oral, rectal, nasal, topical (dermal) or parenteral administration route. Thus, the composition may be in the form of tablets, capsules, suspensions, emulsions, solutions, injectables, suppositories, sprays, aerosols and in other suitable form.

Formulations for oral use include tablets which contain the active ingredient in admixture with non-toxic pharmaceutically acceptable excipients. These excipients may be, for example, inert diluents, such as calcium carbonate, sodium chloride, lactose, calcium phosphate or sodium phosphate; granulating and disintegrating agents, for example, potato starch or alginic acid; binding agents, for example, starch, gelatin or acacia; and lubricating agents, for example, magnesium stearate, stearic acid or talc. Other pharmaceutically acceptable excipients can be colorants, flavouring agents, plasticizers, humectants etc. The tablets may be uncoated or they may be coated by known techniques, optionally to delay disintegration and absorption in the gastrointestinal tract and thereby provide a sustained action over a longer period. For example, a time delay material such as glyceryl monostearate or glyceryl distearate may be employed.

Formulations for oral use may also be presented as chewing tablets, or as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin, or olive oil.

Powders, dispersible powders or granules suitable for preparation of an aqueous suspension by addition of water are also convenient dosage forms of the present invention. Formulation as a suspension provide the active ingredient in admixture with a dispersing or wetting agent, suspending agent and one or more preservatives. Suitable dispersing or wetting agents are, for example, naturally-occurring phosphatides, as e.g. lecithin, or condensation products of ethylene oxide with e.g. a fatty acid, a long chain aliphatic alcohol or a partial ester derived from fatty acids and a hexitol or a hexitol anhydrides, for example, polyoxyethylene stearate, polyoxyethylene sorbitol monooleate, polyoxyethylene sorbitan monooleate etc. Suitable suspending agents are, for example, sodium carboxymethylcellulose, methylcellulose, sodium alginate etc.

The pharmaceutical formulation may also be administered parenterally (intravenous, intramuscular, subcutaneous or the like) in dosage forms or formulations containing conventional, non-toxic pharmaceutically acceptable carriers and adjuvants. The formulation and preparation of such compositions is well-known to those skilled in the art of pharmaceutical formulation. Specific formulation can, however, be found in the text entitled "Remington's Pharmaceutical Sciences" (15).

For parenteral use, the pharmaceutical compositions according to the invention may comprise the thermogenic compounds in the form of a sterile injection. To prepare such a composition, the thermogenic compounds are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution and isotonic sodium chloride solution. The aqueous formulation may also contain one or more preservatives, for example, methyl, ethyl or n-propyl p-hydroxybenzoate.

For the rectal application, suitable dosage forms for a composition according to the present invention include suppositories (emulsion or suspension type), and rectal gelatin capsules (solutions or suspensions). In a typical suppository formulation, the thermogenic compounds are combined with an appropriate pharmaceutically acceptable suppository base such as cocoa butter, esterified fatty acids, glycerinated gelatin, and various water-soluble or dispersible bases like polyethylene glycols and polyoxyethylene sorbitan fatty acid esters. Various additives like e.g. enhancers or surfactants may be incorporated.

For the nasal application typical dosage forms for a composition according to the present invention include nasal sprays and aerosols for inhalation. In a typically nasal formulation, the active ingredients are dissolved or dispersed in a suitable vehicle. The pharmaceutically acceptable vehicles and excipients and optionally other pharmaceutically acceptable materials present in the composition such as diluents, enhances, flavouring agents, preservatives etc. are all selected in accordance with conventional pharmaceutical practice in a manner understood by the persons skilled in the art of formulating pharmaceuticals.

The pharmaceutical compositions according to the invention may also be administered topically on the skin for percutaneous absorption in dosage forms or formulations containing conventionally non-toxic pharmaceutically acceptable carriers and excipients including microspheres and liposomes. The formulations include creams, ointments, lotions, liniments, gels, hydrogels, solutions, suspensions, pastes, plasters and other kinds of transdermal drug delivery systems. The pharmaceutically acceptable carriers or excipients may include emulsifying agents, antioxidants, buffering agents, preservatives, humectants, penetration enhancers, chelating agents, gelforming agents, ointment bases, perfumes and skin protective agents.

Examples of emulsifying agents are naturally occurring gums, e.g. gum acacia or gum tragacanth, naturally occurring phosphatides, e.g. soybean lecithin and sorbitan monooleate derivatives.

Examples of antioxidants are butylated hydroxy anisole (BHA), ascorbic acid and derivatives thereof, tocopherol and derivatives thereof and cysteine.

Examples of preservatives are parabens and benzalkonium chloride.

Examples of humectants are glycerin, propylene glycol, sorbitol and urea.

Examples of penetration enhancers are propylene glycol, DMSO, triethanoiamine, N,N-dimethylacetamide, N,N-dimethylformamide, 2-pyrrolidone and derivatives thereof, tetrahydrofurfuryl alcohol and Azone ®.

Examples of chelating agents are sodium EDTA, citric acid and phosporic acid.

Examples of gel forming agents are Carbopol, cellulose derivatives, bentonit, alginates, gelatin and PVP.

Examples of ointment bases are beeswax, paraffin, cetyl palmitate, vegetable oil, sorbitan esters of fatty acids (Span), polyethyleneglycols, and condensation products between sorbitan esters of fatty acids and ethylene oxide, e.g. polyoxyethylene sorbitan monooleate (Tween).

The formulation and preparation of the above-mentioned compositions is well-known to those skilled in the art of pharmaceutical formulation. Specific formulation can be found in "Remington's Pharmaceutical Sciences" (15).

Preferably, the pharmaceutical composition of the present invention comprises a combination product containing the β adrenergic agonist in combination with the xanthine, i.e. in the case of a tablet, one tablet comprises a mixture of the two active components. However, the pharmaceutical composition of the present invention may also be presented in one package comprising two separate containers, one container comprising a dosage form of the β adrenergic compound and the other container comprising a dosage form of the xanthine compound. In such cases, special instructions for substantially concomitant use of the two drugs should be enclosed with the product. The two dosage forms can be the same or they may be different, preferably the two dosage forms are the same.

The pharmaceutical compositions of the present invention may be used for medical purposes involving administration of a combination of a β adrenergic agent and a xanthine to an animal except a rodent, preferably a mammal, in particular a human.

In one aspect the present invention relates to a method for treatment of overweight or obesity in individuals, in particular in humans or for reducing the adipose tissue mass/lean mass body mass ratio of an individual, in particular a human or a domestic animal.

In the present context the term "overweight" is used as an indication of a body with a weight exceeding the "desirable weight", whereas the term "obesity" is used when the body weight is 20% or more above the "desirable weight". Desirable weights for humans are given by the Council on Scientific Affairs (1) defining the desirable weights for humans according to Metropolitan Height and Weight Tables as the midpoint of the range of the medium-frame individuals.

In another aspect, the present invention relates to a method for the treatment of diseases which are complications to overweight or obesity. These diseases or conditions include diabetes mellitus type II, hypercholesterolemia, hypertriglyceridaemia and hypertension.

In another aspect, the present invention also relates to a method of reducing adipose tissue mass/lean body mass ratio or treating overweight or obesity or complications thereof by means of subjecting the individuals to a diet regimen. The diet regimen into which the individuals may be subjected in connection with the administration of the composition may include a low carbohydrate, a low fat and a low energy regimen, e.g. a diet of from 800–2500 kcal/day.

In a further aspect, the present invention also relates to the use of a combination of a β adrenergic agent and a xanthine for the manufacture of a pharmaceutical composition for the treatment of overweight or obesity or diseases aggravated thereof.

Veterinary use

The compositions according to the invention can also be administered to domestic animals in order to improve the performance of the animal (daily weight gain and feed utilization) or to improve carcass quality or both. Carcass quality is generally improved when the fat tissue mass/lean mass body mass ratio is decreased, i.e. when the body content of meat is increased e.g. at the expense of the body content of fat.

The improvements in performance and carcass quality are suggested to be caused by a reduced fat accretion and/or by an increased skeletal muscle accretion. In growing animals, the amount of lipid present is suggested to be governed by the relative rates of lipolysis and lipogenesis (46). Stimulation of lipolysis and/or inhibition of lipogenesis in fat tissue may lead to a reduced fat accretion. In vivo and in vitro studies with both pigs and ruminants (47–50) may indicate that certain β agonists stimulate lipolysis and inhibit lipogenesis in fat tissue leading to a reduced fat accretion.

Accretion of skeletal muscle may be associated with an inhibition of protein degradation or an increase in protein synthesis. Previous studies have been performed with certain β agonists to elucidate the effect of the β agonist on the protein synthesis or degradation (51, 52) but at present, the exact mode of action on protein accretion is not fully understood.

Administration to an animal of the compositions according to the present invention may be useful in order to increase the lean body mass at the expense of body fat, particularly in domestic animals like pigs, hogs, cattle, sheep and poultry. The composition may be given in admixture with the feed in a suitable dose corresponding to the size of the animal.

Preferably, the composition comprising the combination of the β adrenerg agonist, such as ephedrine hydrochloride, and the xanthine, such as caffeine, is given orally in the form of a powder, the powder being intimately mixed with the dietary powder which is the feed normally consumed by the animal. The dietary powder has a content of protein, fat and vitamins which is normally recommended for optimal growth of the particular animal or the powder may contain a minor surplus of protein so that the animal has a sufficient supply of protein to utilize in case of increase in protein synthesis due to the treatment. The compositions for oral and parenteral use described above may of course also be administered to the domestic animals. The compositions for oral administration can either be given as such or be given in admixture with the dietary feed.

The weight ratio between the β adrenerg agonist and the xanthine is in general from about 1:8 to about 1:24, preferably from about 1:8 to about 1:20, especially from about 1:8 to about 1:18, in particular from about 1:10 to about 1:16, such as about 1:12. However, the ratio which gives optimal effect (i.e. a synergistic or a supra-additive effect of the β adrenerg agonist and the xanthine) may vary in relation to the specific compound and the particular animal species.

The daily amount of the combination of the β adrenerg agonist and the xanthine is dependent on the route of administration and the animal species being treated. In general, a daily dose of ephedrine hydrochloride can be about 0.005–50 mg per kg body weight, preferably about 0.05–20 mg per kg body weight, and the daily dose of caffeine is about 0.04–1200 mg per kg body weight, preferably 0.5–500 mg per kg body weight.

The ratio of fat tissue mass/lean mass body mass is defined as the weight of the body content of fat divided by the weight of the body content of meat after dissection of the carcass of the particular animal.

A growing bull having a weight of e.g. 456 kg in general comprises about 174 kg meat, about 31 kg fat and about 45 kg bones. The ratio fat tissue mass/lean mass body mass is thus about 0.17. Correspondingly, a pig having a weight of e.g. 90 kg, normally comprises about 35 kg meat, about 20 kg fat and about 7 kg bones. Thus, the ratio for the pig is 0.57. The normal ranges of the fat tissue mass/lean mass body mass is thus dependent of the particular animal species and an improvement of carcass quality can be expressed as a decrease of the ratio values compared to the normal ratio values for the animal in question. In general, a decrease corresponding to at least 5%, preferably at least 10% from the normal ratio values can be expected after oral administration of the combination of ephedrine and caffeine.

BRIEF DESCRIPTION OF THE DRAWING

The invention is further described with reference to the drawings.

Figure 1A:
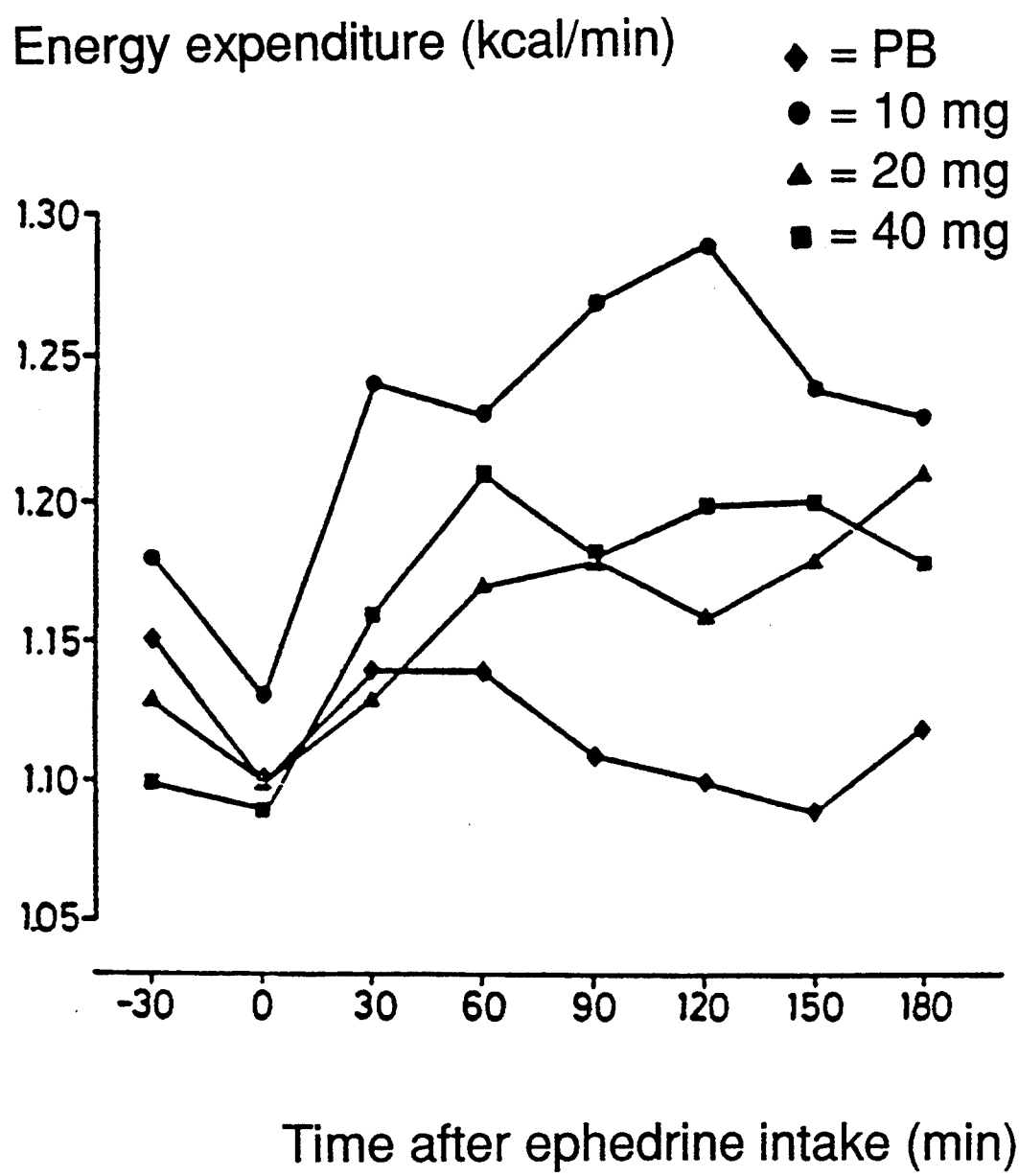
FIG. 1: A. Changes in energy expenditure and B. the integrated responses above baseline after different doses of ephedrine hydrochloride and placebo (PB=placebo).

The invention is further disclosed in the following non-limiting examples:

EXAMPLES

EXAMPLE 1A

Preparation of capsules containing ephedrine and caffeine

Capsules containing ephedrine and caffeine were prepared from the following ingredients:

| | |
|---|---|
| Ephedrine hydrochloride Ph. Eur. | 20 mg |
| Caffeine Ph. Eur. | 200 mg |
| Lactose Ph. Eur. | approx. 90 mg |

The amounts given are per capsule.

The ingredients were sieved, mixed and filled in gelatine capsules using conventional pharmaceutical methods for preparation of capsules.

EXAMPLE 1B

Preparation of tablets containing ephedrine and caffeine

Tablets containing ephedrine and caffeine were prepared from the following ingredients shown in Table 1 using conventional, pharmaceutical methods for manufacturing tablets including a wet-granulation:

TABLE 1

Composition of ephedrine/caffeine combination tablets prepared using a wet-granulation method

| Ingredient | Quantity per tablet (mg) | Function | Reference |
|---|---|---|---|
| Ephedrine hydrochloride | 20 | Active ingredient | Ph. Eur. |
| Caffeine | 200 | Active ingredient | Ph. Eur. |
| Hydrochloric acid 2M | 0.75 | pH-adjuster | Ph. Nord. 63 |
| Magnesium stearate | 1.6 | Lubricant | Ph. Eur. |
| Glycerol (85 per centum) | 2 | Humectant | Ph. Eur. |
| Gelatine | 2.5 | Binder | Ph. Eur. |
| Talc | 14.4 | Lubricant | Ph. Eur. |
| Purified water | 15 | Solvent | Ph. Eur. |
| Ethanol (94.6–96.4% v/v)* | 31.8 | Solvent | DLS |
| Potato starch | 124 | Filler | Ph. Eur. |

*Disappears during manufacturing

If desired, the tablets may be coated by conventional methods in a subsequent stage.

EXAMPLE 1C

Preparation of tablets containing ephedrine and caffeine

Tablets containing ephedrine and caffeine were prepared from the following ingredients shown in Table 2 using conventional pharmaceutical methods for preparation of tablets by direct compression.

TABLE 2

Composition of ephedrine/caffeine combination tablets prepared by direct compression

| Ingredient | Quantity per tablet (mg) | Function | Reference |
|---|---|---|---|
| Ephedrine hydrochloride | 20 | Active ingredient | Ph. Eur. |
| Caffeine | 200 | Active ingredient | Ph. Eur. |
| Magnesium stearate | 0.25 | Lubricant | Ph. Eur. |
| Propylenglycol | 0.7 | Plasticizer | Ph. Eur. |
| Talc | 2.3 | Filler | Ph. Eur. |
| Titanium dioxide | 2.3 | Colouring agent | Ph. Eur. |
| Methylhydroxypropyl-cellulose 15 | 3.5 | Film former | Ph. Eur. |
| Potato starch | 11 | Filler | Ph. Eur. |
| Microcrystalline cellulose | 64 | Filler | Ph. Eur. |
| Purified water* | 66.3 | Solvent | Ph. Eur. |

*Disappears during manufacturing

If desired, the tablets may be coated by conventional methods in a subsequent stage.

EXAMPLE 2

A dose-response study of the thermogenic effect of caffeine, ephedrine, separately and in combinations The study was carried out at The Institute of Medical Physiology C, Panum Institute, University of Copenhagen, Denmark.

Aim

The purpose of the present study was to examine the relation between selected doses of caffeine, ephedrine and combinations thereof, and the thermogenic, cardiovascular and metabolic effects.

Study design

The study was conducted in two parts. The first part was designed as a placebo-controlled, double-blind trial on the effect of 3 different doses of caffeine, 3 different doses of ephedrine and 2 placebo samples. The order of the tests were not entirely randomized, but organized in a sequence that allowed testing for a carry-over effect.

Based on the results from the first part, 3 combinations of different doses of caffeine and ephedrine were chosen and tested in the second part which was designed as a randomized, double-blind study.

The volunteers were the same in the two parts of the study, and this design allowed direct comparison of the data from the two trials, regarding all tests as randomized blocks without introducing any bias.

Subject Selection 6 healthy volunteers of normal weight (3 of each sex) aged between 20 and 32 were included after informed consent was obtained. The average age of the 6 volunteers was 25 ($\pm 1$) years, height, 179 ($\pm 11$) cm; body weight, 70 ($\pm 13$) kg; percentage of overweight, $-1.7$ ($\pm 8.3$) % and body fat, 13 ($\pm 3$) kg. The numbers in parenthesis are the standard deviation. The percentages of overweight was calculated from the individual body weight (IBW) using the midpoint of the medium frame (MMF) given in the Metropolitan Life Insurance Company tables of desirable weights (1):

$$\% \text{ overweight} = \frac{IBW - MMF}{MMF} \times 100\%$$

An estimate of the body fat content was obtained from duplicate measurements of the biceps, triceps, subscapular and suprailiac skin folds with a Harpender caliper on two separate days (16).

Excluded were subjects with a habitual intake of more than 1-2 daily cups of coffee ($>100-200$ mg of caffeine). The volunteers were not allowed to take any medicine during the study apart from the trial medication.

All 6 volunteers completed the study.

Treatment administered

A. Treatment with ephedrine comprising capsules with 10 mg, 20 mg or 40 mg of ephedrine hydrochloride, respectively.

B. Treatment with caffeine comprising capsules with 100 mg, 200 mg or 400 mg of caffeine, respectively.

C. Treatment with a combination of ephedrine and caffeine comprising capsules made according to Example 1A with the following amounts of ephedrine hydrochloride and caffeine: (20 mg+200 mg), (20 mg+100 mg) and (10 mg+200 mg), respectively.

D. Treatment with placebo capsules without active drug(s).

All capsules were identical with regard to appearance and taste, and lactose was used as an inactive filler.

The capsules were administered orally as single doses and swallowed with 300 ml of tap water (20° C.).

Study Plan

Each volunteer received all treatments. There was a minimum of three days between two consecutive tests.

Before starting the tests, the volunteers were instructed to abstain from consuming food and caffeine containing stimulants such as coffee, tea and smoking, at least 12 hours before the tests. Furthermore, no physical activity was allowed before the tests.

The intake of the test substance was supervised and the compliance was controlled by measurement of plasma concentrations of methylxanthine metabolites before and after intake. The resulting baseline values of these analyses were used to verify that the volunteers abstained from intake of caffeine contained in food products or stimulants in accordance with the protocol.

Prior to the study, the volunteers (experimental subjects included in the study) were getting used to the experimental procedures to prevent hyperventilation etc.

At least 60 minutes before the beginning of the study, a green Venflon catheter was inserted percutaneously into an antecubital vein for blood sampling. The catheter was kept open during the study by flushing with isotonic sodium chloride solution (154 mmol/l) after each sampling. The room temperature was kept constant at 25°-27° C.

During the study, the subjects rested supine but sleeping was not permitted. No movements or changes in position were allowed in order to avoid any influence of physical activity on energy expenditure and catecholamine levels.

All blood samples for determination of substrate, metabolite and hormone concentrations were collected form the antecubital vein. Blood samples were taken at $-30$, 0, 30, 60, 90, 120, 150 and 180 minutes relative to the capsule intake (time 0). The subjects breathed through a low-resistance Scuba one-way mouthpiece. After about 10 minutes of adaptation, expiratory gas was collected in Douglas bags for 10 minute periods. Gas collection was made after each blood sampling.

Effect Evaluation

Energy Expenditure

Energy expenditure of man can be measured with great accuracy by direct calorimetry. This requires, however, a very expensive apparatus and cannot be used to assess the short term effect of thermogenic agents because of the changes in heat storage within the body (17). Indirect calorimetry (measurement of oxygen consumption and carbon dioxide elimination) and direct calorimetry give almost identical results in a resting man under conditions of thermal comfort and stability (17). It has been demonstrated that indirect calorimetry is a very accurate technique, since the reproducibility in oxygen consumption and carbon dioxide elimination is very high. In addition, a comparison of different techniques of indirect calorimetry shows that the ventilated hood, face mask, and mouthpiece give similar results (18). The coefficient of variation for resting energy expenditure at a one day interval and a one week interval was found to be 2.4% and 2.2% by the technique described below.

Energy expenditure was measured by indirect calorimetry. Expiratory gas was continuously analyzed for the content of oxygen and carbon dioxide with a Godart Rapox Oxygenmeter and a Beckman LB-1 Medical Gas Analyzer. Respiratory steady state was assumed to be present, when the end-expiratory carbon dioxide fraction was constant. Expiratory gas was collected in Douglas bags and analyzed for the content of oxygen and carbon dioxide with Radiometer gas-electrodes connected to an acid-base analyzer (PHM 71, Copenhagen, Denmark), and the volume of expiration gas was measured with a gas meter. In order to obtain accurate results with low coefficients of variation, the gas electrodes were suitably calibrated with standard gasses of a known composition before use, i.e. prior to every sampling for gas analysis. The standard gasses were analyzed with a Scholander microtechnique with a measuring error on gas fraction being <0.0005%, i.e. the error on measurement of expired gas being within ±0.1–0.2% (19). The apparatus used in the present investigation was shown to have a coefficient of variation on repeated hourly measures of ≦3%. A fixed protein catabolism was assumed, since the error on calculating the energy expenditure by omitting the exact correction from urinary nitrogen was negligible (20). The energy expenditure was calculated taking de novo lipogenesis into account (21).

Laboratory Methods

Through the indwelling antecubital cannula, blood was sampled without stasis in iced syringes. The blood samples were then centrifuged at 4° C. and nonesterified fatty acids (NEFA) were immediately extracted from the blood samples and later determined as described in (22). The concentration of glucose in plasma was determined using the glucose oxidase method (23), the concentration of glycerol in plasma was determined as described by Laurell and Tibbling (24), the concentration of lactate in plasma was described using the method described by Noll (25), and the concentration of triglyceride in plasma was determined as described by Giegel (26). Blood samples for the determination of methylxanthine metabolites was collected in tubes containing reduced glutathione and ethylene glycol-bis($\beta$-aminoethyl)-N,N,N',N'-tetraacetic acid (EGTA). Samples were immediately centrifuged and the plasma was stored at −40° C. until the determination of methylxanthines was performed (see Example 4). Immunoreactive insulin, pancreatic glucagon and C-peptide concentrations were measured in the plasma samples using radioimmunoassay kits purchased from Novo, Copenhagen. All plasma aliquots for determination of pancreatic hormones and methylxanthine metabolites were coded and analyzed in a random order to avoid any systematic error due to the order of analysis. The concentrations of sodium and potassium in the plasma samples were determined by flame spectrophotometry.

Safety Evaluation

Arterial blood pressure was measured in the right arm by a sphygmomanometer a.m. Riva-Rocci, and heart rate was determined by palpation of the peripheral heart rate in the ipsilateral radial artery. These measurements were performed after each sampling of blood.

A "Trimline" apparatus manufactured by PyMaH (Copenhagen) was used to measure the arterial blood pressure. A cuff 12–14 cm in width was employed. The manometer pressure was slowly and gradually reduced from 200 mmHg and the first Korotkoff sound was registered as the systolic pressure. The diastolic blood pressure was determined as the manometer pressure when the Korotkoff sound quality changes from tapping to muffled.

At the end of each study comprising oral administration of the actual test substance, subjective feelings of side-effects were assessed by questioning the experimental subjects.

Statistical Analyses

The responses to a test substance were estimated separately for each subject as the difference between the integrated numerical area of the response curve (by a trapezoidal approach) and the rectangular area determined by the basal values. To estimate the predictive, theoretical effect of combinations of ephedrine and caffeine, the single dose responses were added after subtracting the average placebo response. This calculation was performed separately for each subject before statistical analysis. A two-way analysis of variance for randomized blocks was performed (28) to test differences between experimental periods within the same experiment and to test differences between the responses to different stimuli (test substances). Post-hoc testing was applied to compare two means (28). A possible carry-over effect was evaluated by comparing data obtained from the two placebo periods by means of a paired t-test. A value of $P<0.05$ was considered to be significant. Linear regression and correlation analyses were performed with standard methods (28). All results are expressed as mean±standard error of the mean (SE).

There was no protocol deviations or drop-outs.

Results

Effect Evaluation

Energy Expenditure and Respiratory Quotient

The baseline energy expenditure in the two placebo tests were 1.10±0.08 kcal/min and 1.09±0.10 kcal/min, respectively. The coefficient of day-to-day variation was 2.4%. In Table 3 is shown the thermogenic effect expressed as the mean energy expenditure of the two placebo tests during 3 hours of study, the mean energy expenditure being calculated as the area under the curve and the pre-administration values being the baseline values (i.e. the integrated responses to placebo are given in Table 3).

TABLE 3

| The average individual thermogenic response to placebo | |
|---|---|
| Subjects[a] | Energy Expenditure (kcal/3 h) |
| 1 | 9.9 |
| 2 | −4.4 |
| 3 | −13.4 |
| 4 | 12.6 |
| 5 | 19.5 |
| 6 | 12.7 |
| Mean ± SE | 6.2 ± 5.1 |

[a]Individual results are given as average of the two placebo tests

Ephedrine

Figure 1B:
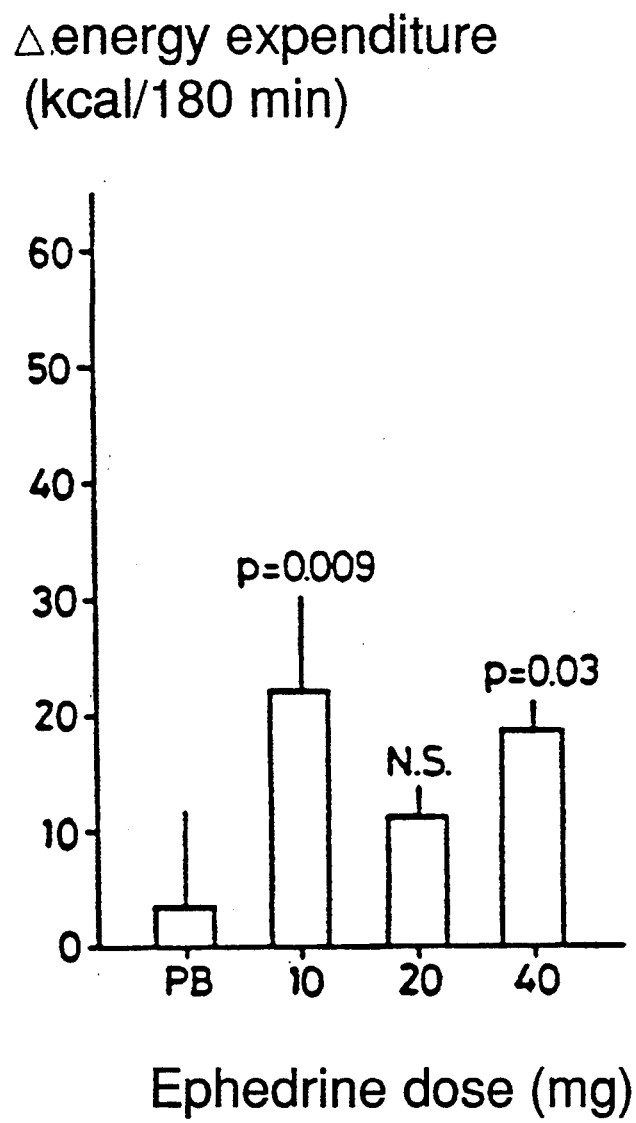

The changes in energy expenditure and in the integrated responses above baseline after oral administration of different doses of ephedrine hydrochloride and placebo are shown in FIG. 1. In average, the energy expenditures after administration of 10, 20 and 40 mg of ephedrine hydrochloride were 16.0±10.9 kcal/3 h (p=0.016), 6.3±5.3 kcal/3 h (not significant) and 12.1±4.9 kcal/3 h (p=0.05), respectively, greater than placebo. The ratios of energy expenditure between the different treatments and placebo are given in Table 4.

Table 4

Mean energy expenditure during 3 hours of study after treatment with placebo, ephedrine hydrochloride, caffeine or a combination of ephedrine hydrochloride and caffeine

TABLE 4

Mean energy expenditure during 3 hours of study after treatment with placebo, ephedrine hydrochloride, caffeine or a combination of ephedrine hydrochloride and caffeine

| Treatment | Mean energy expenditure kcal/3 h | Energy expenditure/ (placebo value) |
|---|---|---|
| Placebo | 6.2 | 1 |
| Ephedrine[a)] | | |
| 10 mg[b)] | 22.2 | 3.5 |
| 20 mg[b)] | 12.5 | 2.0 |
| 40 mg[b)] | 18.3 | 3.0 |
| Caffeine | | |
| 100 mg | 15.4 | 2.5 |
| 200 mg | 13.4 | 2.2 |
| 400 mg | 38.6 | 6.2 |
| Ephedrine and caffeine | | |
| (10 + 200) mg | 16.6 | 2.7 |
| (20 + 100) mg | 13.9 | 2.2 |
| (20 + 200) mg | 24.0 | 3.9 |

[a)]Administered in the form of ephedrine hydrochloride
[b)]The dose given as mg of ephedrine hydrochloride These values are minimum figures as the energy expenditure had not returned to baseline value 3 hours after the intake. Furthermore, no obvious relation between dose and thermogenic response was found.

Caffeine

Figure 2A:
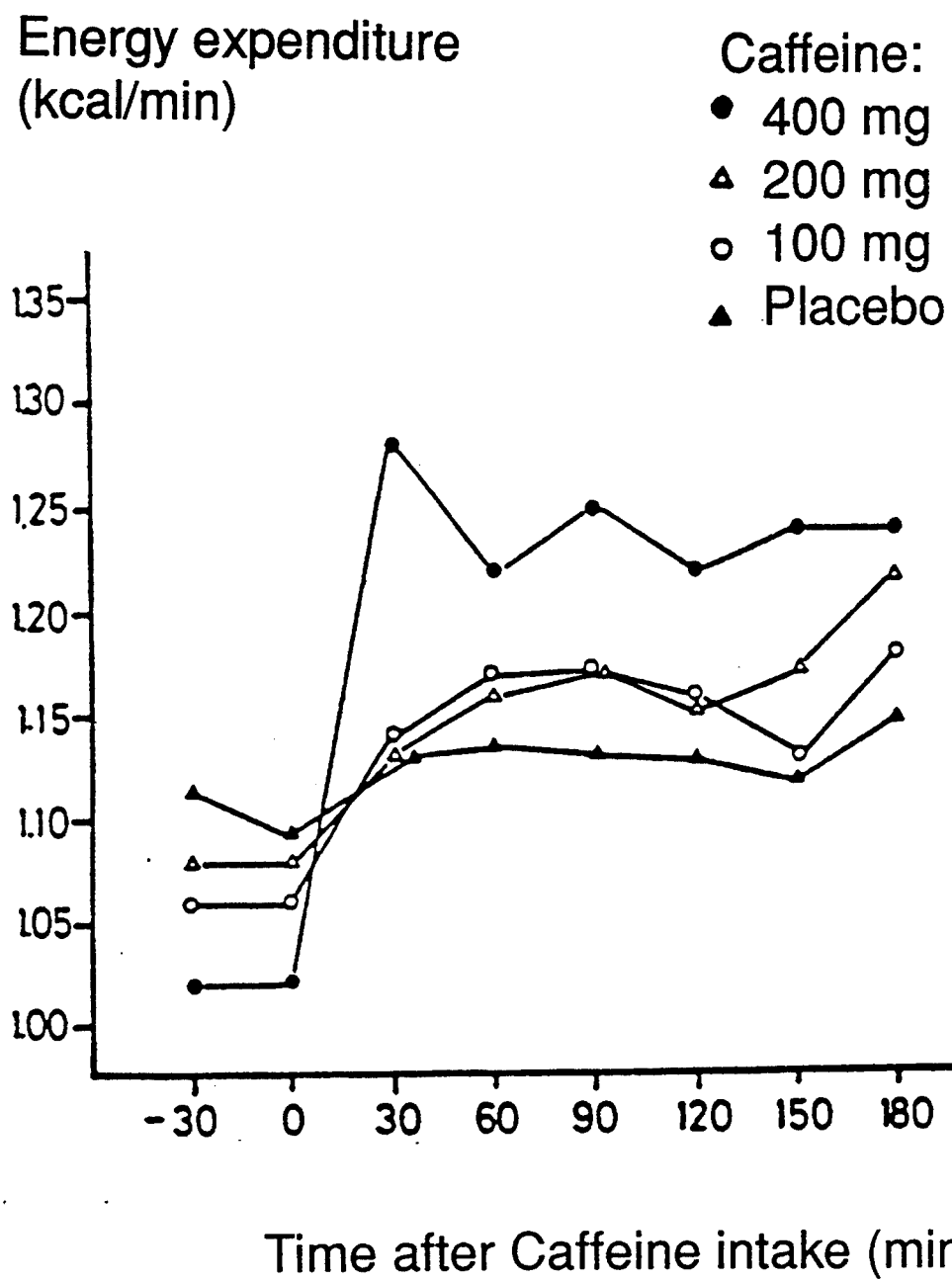
FIG. 2: A. Changes in energy expenditure and B. the integrated responses above baseline after different doses of caffeine and placebo.
Figure 2B:
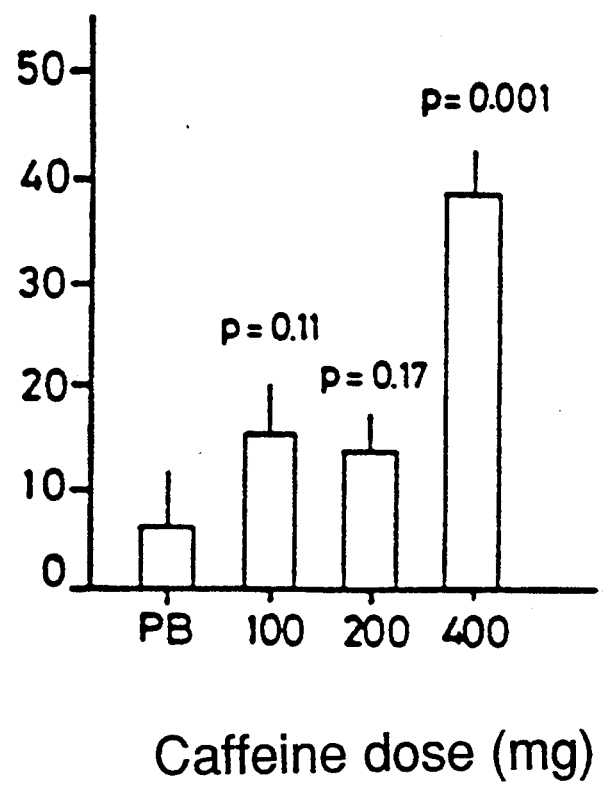

The changes in energy expenditure and in the integrated responses above baseline after oral administration of different doses of caffeine and placebo are shown in FIG. 2. In average, the energy expenditures after administration of 100, 200 and 400 mg of caffeine were $9.2 \pm 5.7$ kcal/3 h (p=0.11), $7.2 \pm 6.0$ kcal/3 h (p=0.17) and $32.4 \pm 8.2$ kcal/3 h (p<0.001), respectively, greater than placebo (Table 4). As described above, these values are minimum figures as the energy expenditure had not returned to baseline value 3 hours after the intake. Linear regression analysis showed a significantly linear relation between the caffeine dose and the integrated response above baseline of plasma concentration of caffeine, the pre-administration value being the baseline value, p=0.000015. Similarly, a significant relation between caffeine dose and thermogenic response (energy expenditure) (p=0.006) was found.

Combinations of Ephedrine and Caffeine

Figure 3:
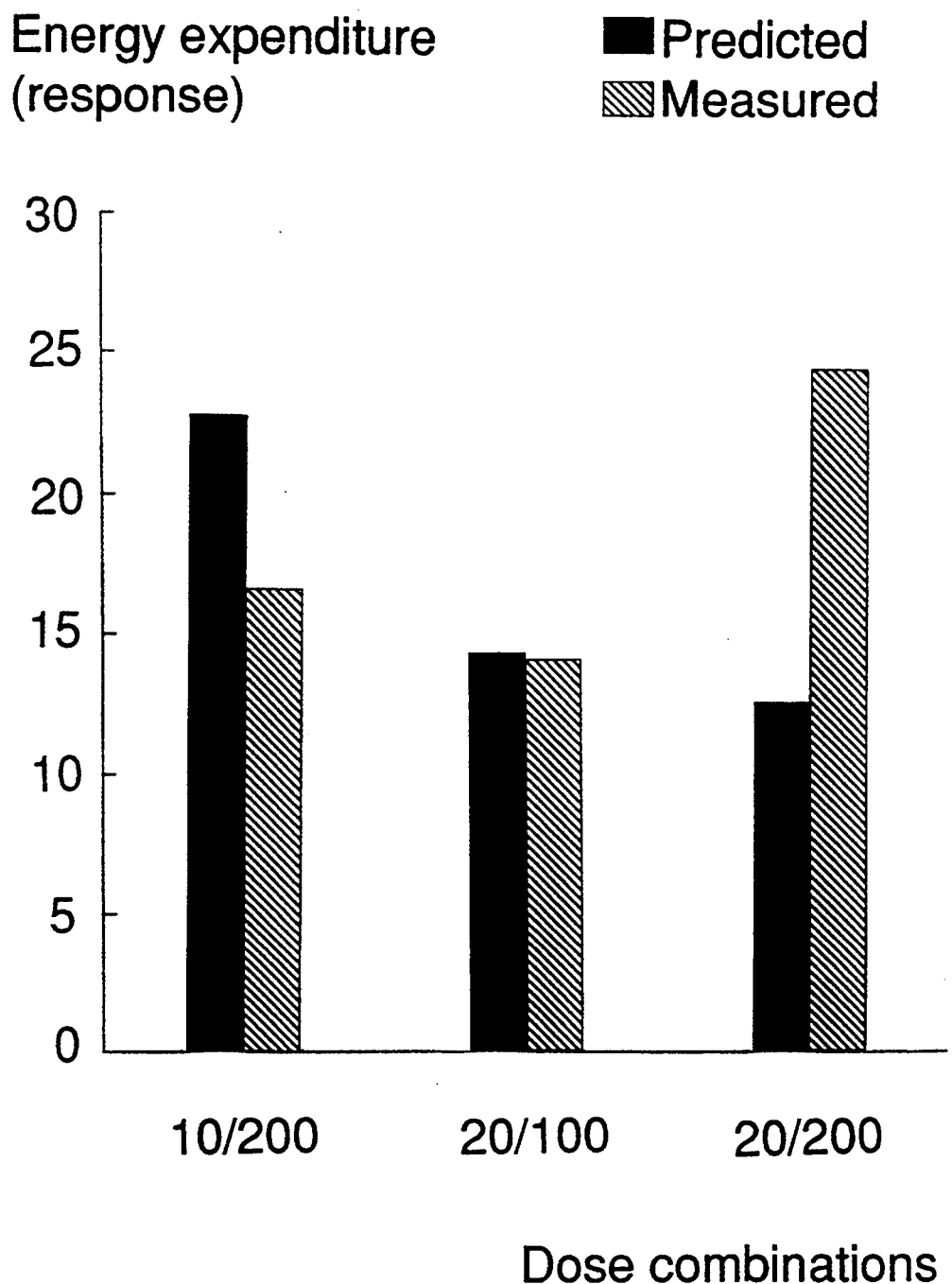
FIG. 3: The predicted and actually measured thermogenic effect of a pharmaceutical composition of a combination of ephedrine and caffeine, according to Examples 2 and 3. Dose combinations are given as mg ephedrine hydrochloride/mg caffeine.
Figure 4A:
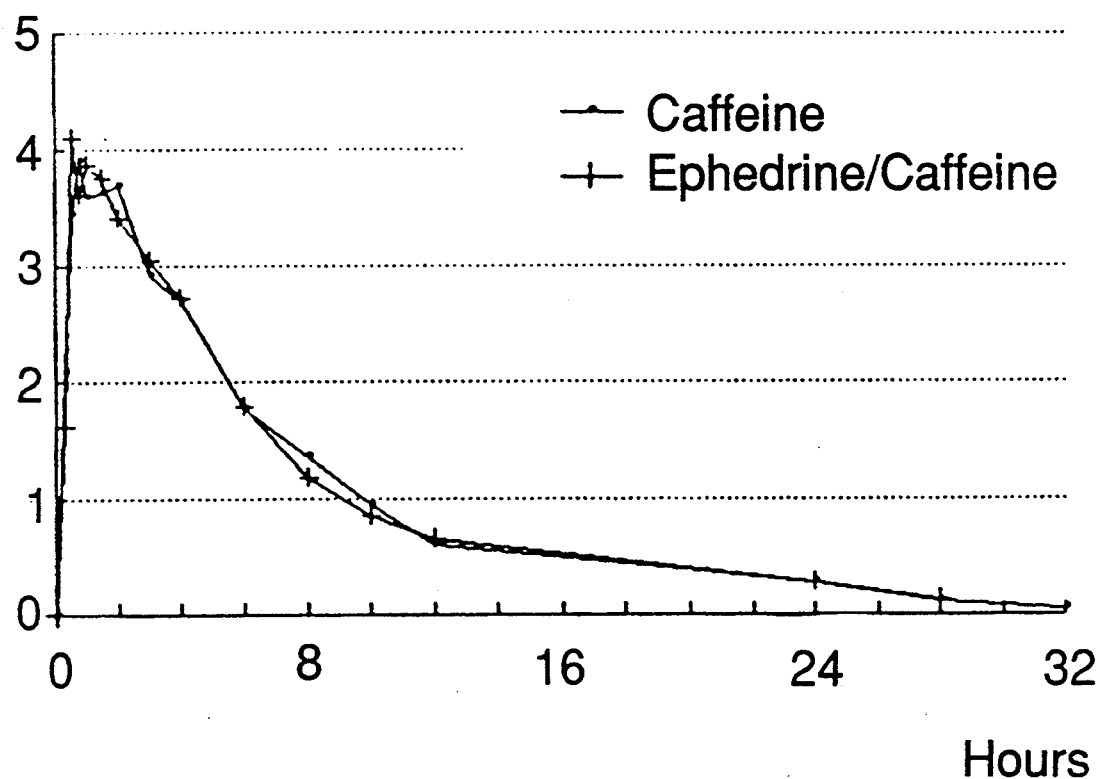
FIG. 4: Median serum concentration values of caffeine (FIG. 4A), theobromine (FIG. 4B) and paraxanthine (FIG. 4C) ($\mu$g/ml) after administration of caffeine tablets 200 mg and ephedrine/caffeine combination tablets 20/200 mg, respectively, to 12 volunteers, and median curve of the excretion rate of ephedrine (FIG. 4D) after administration of ephedrine tablets 20 mg (—x—) and ephedrine/caffeine combination tablets 20/200 mg, respectively, to 12 volunteers.
Figure 4B:
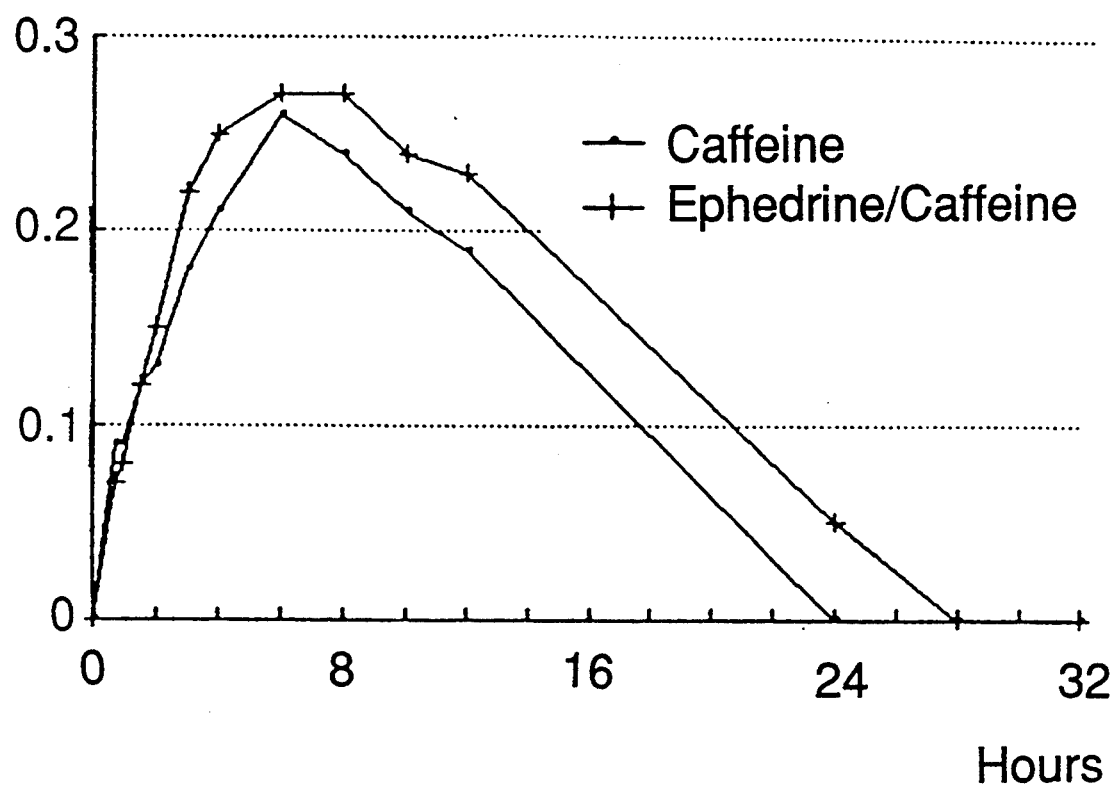
Figure 4C:
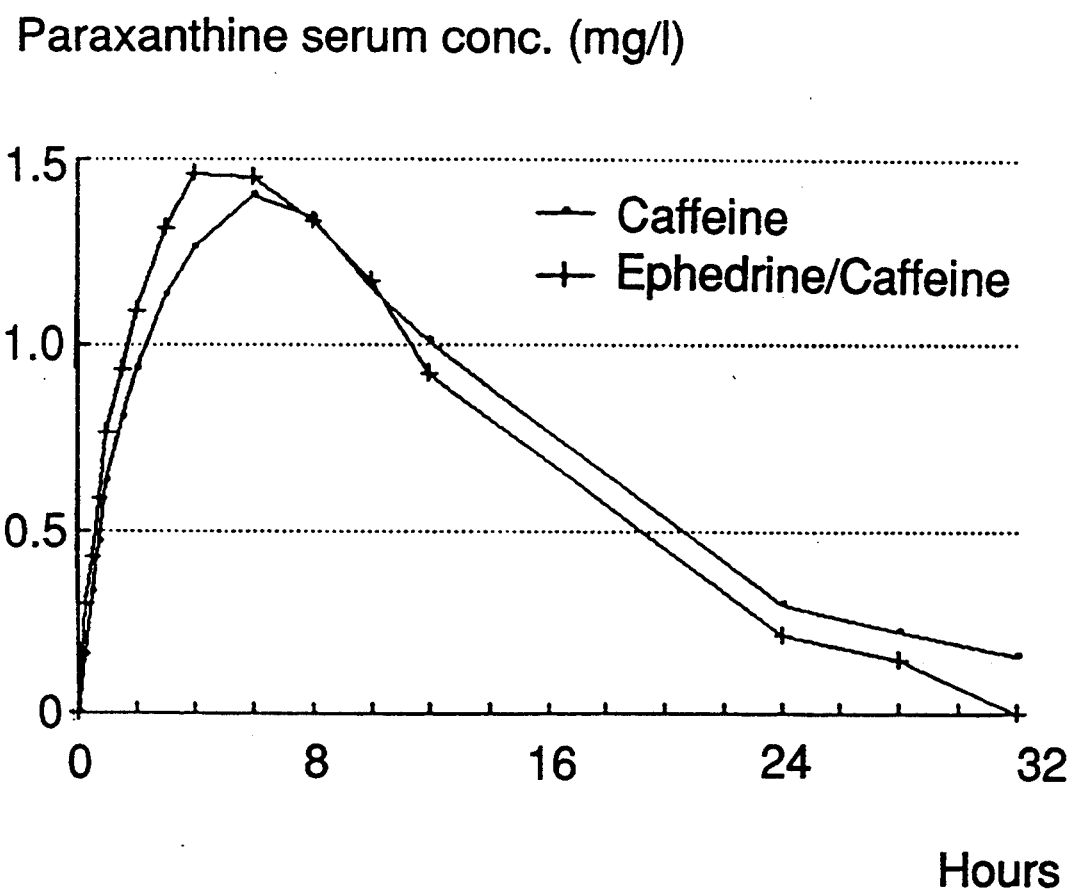
Figure 4D:
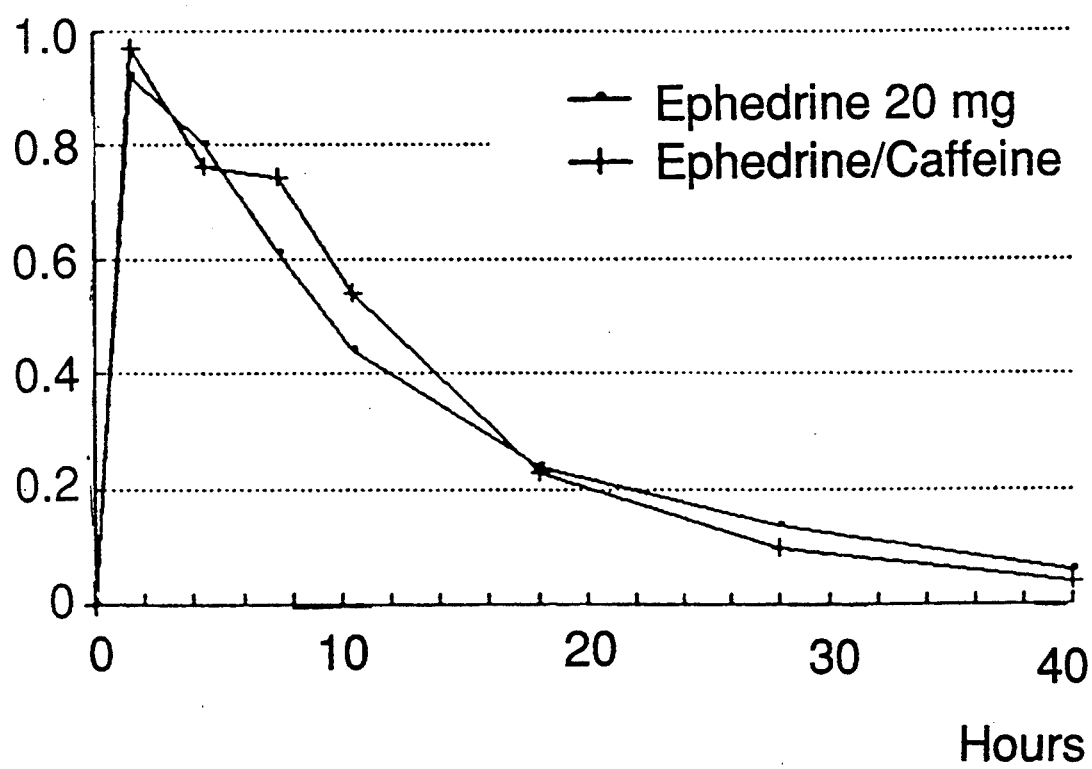

The changes in the integrated responses above baseline after different doses of combinations of ephedrine and caffeine are shown in FIG. 3. In average, the energy expenditure after administration of (10 mg and 200 mg), (20 mg and 100 mg) and (20 mg and 200 mg), respectively, in doses of ephedrine/hydrochloride and caffeine were $16.6 \pm 7.4$ kcal/3 h, $13.9 \pm 2.7$ kcal/3 h and $24.0 \pm 8.6$ kcal/3 h, respectively, greater than placebo (Table 4). These values are minimum figures as the energy expenditure had not returned to baseline value 3 hours after intake.

Based on the results from separate administration of ephedrine and caffeine, respectively, a predicted thermogenic response (energy expenditure) relating to oral administration of the combination can be calculated for each volunteer as the individual thermogenic effect of the $\beta$ agonist (ephedrine) plus the individual thermogenic effect of methylxanthine (caffeine) determined separately minus two times the thermogenic effect of placebo. In table 5 are given the predicted and actual placebo-corrected thermogenic responses. Placebo-correction is made by subtracting the placebo value from the total thermogenic response caused by the actual treatment.

TABLE 5

Placebo and actual placebo-corrected thermogenic responses (kcal/3 h) to different combinations of ephedrine[a)] and caffeine doses (mg)

| Subject no. | Predicted response | | | Actual response | | |
|---|---|---|---|---|---|---|
| | 10/200[d)] | 20/100[d)] | 20/200[d)] | 10/200[d)] | 20/100[d)] | 20/200[d)] |
| 1 | 20.8 | 16.3 | 4.2 | −18.9 | 3.2 | 12.9 |
| 2 | 77.8 | 29.4 | 44.8 | 34.5 | 11.7 | 33.3 |
| 3 | 47.3 | 45.8 | 44.7 | 22.5 | 19.6 | 55.9 |
| 4 | −28.2 | 19.1 | −21.5 | 18.5 | 19.8 | −2.6 |
| 5 | −14.3 | −12.3 | −1.4 | 21.4 | 18.6 | 9.9 |
| 6 | 32.0 | −2.7 | 2.9 | 21.3 | 10.3 | 34.0 |
| X[b)] | 22.6 | 14.3 | 12.3 | 16.6 | 13.9 | 24.0 |
| SE[c)] | 16.0 | 8.8 | 10.9 | 7.4 | 2.7 | 8.6 |
| p[*)] | — | — | — | NS | NS | −0.02 |

[a)]as ephedrine hydrochloride
[b)]mean
[c)]standard error
[d)]the notation 10/200 indicates that the composition contains 10 mg ephedrine hydrochloride and 200 mg caffeine
[*)]p values denote statistical difference between predicted and actual measured placebo-corrected thermogenic response.

A comparison between the predicted and the measured responses shows that the combinations 10/200 and 20/100 had similar or slightly lower thermogenic effect than anticipated. These differences were, however, not significant. But there is evidently a supra-additive thermogenic effect (see Example 3 for definition of supra-additive thermogenic effect) after administration of the 20/200 combination, as the measured effect ($24.0 \pm 8.6$ kcal/3 h), was significantly higher than expected ($12.3 \pm 10.9$ kcal/3 h, p=0.02). A much lower standard error was observed in the mean values measured compared with the predicted values.

In conclusion, ephedrine, caffeine and combinations thereof possess thermogenic activity. A supra-additive thermogenic effect was demonstrated after oral administration of a composition of the combination of ephedrine and caffeine, the composition containing 20 mg ephedrine hydrochloride and 200 mg caffeine, whereas only an additive effect was found for the compositions of two other combinations of ephedrine and caffeine (10/200 and 20/100) respectively.

Furthermore, the respiratory quotient decreased slightly in all experiments indicating that the energy expenditure induced by the drugs were due to an increased carbohydrate and lipid oxidation.

Safety Evaluation
Side Effects

The incidence of side effects after administration of the active compounds and placebo, respectively, was not significant, except for caffeine 400 mg (p<0.01)

which was then excluded prior to the second part of the study. Ephedrine hydrochloride given in a dose corresponding to 40 mg was also excluded due to excessive increase in systolic blood pressure and heart rate. Thus, no serious side effects of the treatments were observed apart from treatments with caffeine 400 mg and ephedrine hydrochloride 40 mg.

Laboratory methods

Influential changes for all treatments were only observed for the values concerning serum glucose, serum nonesterified fatty acids (NEFA) and glycerol.

Serum glucose

Compared to placebo, oral administration of ephedrine as well as caffeine resulted in a hyperglycemic effect. This effect was most and equally pronounced for ephedrine hydrochloride 20 and 40 mg. The compositions of the combinations of ephedrine and caffeine had effects which were not significantly different from the predicted effects and the 20/200 combination showed the most marked response.

Serum nonesterified fatty acids and glycerol

Oral administration of ephedrine and caffeine and the combinations thereof increased the concentrations of NEFA and glycerol in the serum, probably resulting from an increased lipolysis induced by fasting.

In summary:
1. Both ephedrine and caffeine possess thermogenic activity, and
2. the thermogenic effects of ephedrine and caffeine are potentiated after oral administration of a pharmaceutical composition of a combination of ephedrine and caffeine comprising 20 mg ephedrine hydrochloride and 200 mg caffeine, the specific combination showing a supra-additive thermogenic activity.

EXAMPLE 3

Conditions to be fulfilled for a synergistic interaction to be supra-additive

To recognize a supra-additive thermogenic effect (SAE) of a combination of two compounds, actual measurements of the thermogenic effects of the compounds should be performed separately and in combination in healthy volunteers. The testing should be carried out in double-blind, placebo controlled design.

Definitions $$SAE = \frac{\text{Actual effect of combination } (AEC)}{\text{Predicted effect of combination } (PEC)} > 1.0$$

AEC: Measured thermogenic effect of combination of a $\beta$ agonist (e.g. ephedrine) and a methylxanthine (e.g. caffeine) minus the placebo response. The thermogenic effect is the integrated increase in energy expenditure above baseline for at least 3 hours after the intake.

PEC: Thermogenic effect of the $\beta$ agonist (e.g. ephedrine) plus thermogenic effect of the methylxanthine (e.g. caffeine) determined separately minus two times the thermogenic effect of placebo.

The statistical evaluation is performed by a two-way analysis of variance for repeated measures i.e. AEC->PEG so the repeated measures are 3, given 2 degrees of freedom. Level of significance, p<0.05 by a two-sided testing.

The actual value of SAE in percentage can be calculated by the following equation:

$$SAE (\%) = \frac{(AEC - PEC) \times 100\%}{|PEC|}$$

where |PEC| in the denominator is the numerical value of PEC.

By treating the data from Table 5 in Example 2 according to the above definition, the following Table 6 is obtained, and the figures are shown in FIG. 3.

TABLE 6

Supra-additive thermogenic effect (SAE) of a pharmaceutical composition of a combination of ephedrine hydrochloride and caffeine. The values shown are the mean-values from 6 treated volunteers of normal weight

| Treatment[a] | AEC | PEC | SAE | SAE (%) |
|---|---|---|---|---|
| 10/200 | 16.6 | 22.6 | 0.73 | −26.5 |
| 20/100 | 13.9 | 14.3 | 0.97 | −2.7 |
| 20/200 | 24.0 | 12.3 | 1.95 | 95.0 |

[a]given in mg ephedrine hydrochloride/mg caffeine

By statistical analysis, significance was found for the 20/200 combination (p=0.02)

EXAMPLE 4

Bioavailability study of ephedrine/caffeine combination tablets versus ephedrine tablets and caffeine tablets in healthy volunteers The study was carried out at DAK-Laboratoriet, Copenhagen.

Aim

The aim of this study was 1) to compare the amount of ephedrine and caffeine absorbed from an ephedrine/caffeine combination tablet to the absorption from the single drug tablets (ephedrine tablet and caffeine tablet, respectively) and 2) to compare the kinetic parameters such as $T_{\frac{1}{2}}$ (biological half-life), $T_{max}$ (time for maximum drug plasma concentration) and $C_{max}$ (maximum drug concentration) after oral administration of the different tablets in order to kinetically evaluate possible drug interactions after simultaneous administration of ephedrine and caffeine in a combination tablet.

Study Design

The study was performed as an open, randomised, cross-over trial. The volunteers were separated in 2 blocks of 6. Each volunteer received the three different tablets as single doses with an interval of at least 6 days.

Volunteers 13 healthy adult volunteers were included in the study. One volunteer did not want to continue after the first study day because of suspected caffeine abstinence symptoms. 12 volunteers completed the study (3 male and 9 female), median age 37 years (range 28–42 years), median weight 66 kg (range 50–82 kg) and median height 167 cm (range 159–179 cm). All the volunteers gave their informed consent. 4 volunteers smoked about 20 cigarettes/day, 1 smoked 1–3 cigarettes/day and 7 did not smoke at all.

The following exclusion criteria were used:

Pregnant or lactating women or women wishing to become pregnant.

Volunteers receiving chronic medications, including oral contraceptives but excluding vitamins and minerals.

Volunteers with known allergy to any of the compounds in the tablets.

Volunteers with acute or chronic diseases which could influence
  a) the health of volunteer, b) the study,
as judged by the responsible investigator.

Volunteers who had donated blood within two weeks prior to the investigation.

Volunteers who were suspected to be non-compliants.

Volunteers with clinically significant abnormalities in the pre-study laboratory measurements.

Before treatment, one of the investigators examined all volunteers using routine procedures, including blood pressure, heart rate and ECG measurements. Blood samples for the following laboratory tests were taken: Haemoglobin, leucocytes, ASAT, LDH, alkaline phosphates, amylase, and creatinine. A urine sample was checked for sugar, blood and albumin by a qualitative test.

The following normal ranges for the laboratory values were used: Haemoglobin: Male 8–11 mmol/l, female 7–10 mmol/l; leucocytes: $3-9 \times 10^9$/l; ASAT: 10–40 U/l; LDH: 200–450 U/l; alkaline phosphates: 50–275 U/l; amylase: 70–300 U/l; and creatinine: 60–130 $\mu$mol/l.

All the volunteers were judged as being in good health by the physician and their laboratory values were within the normal range.

None of the volunteers were excluded by the exclusion criteria.

Treatment Administered

A: Caffeine tablets 200 mg, DAK containing 200 mg of caffeine per tablet.

B: Ephedrine tablets 20 mg, DAK, containing 20 mg of ephedrine hydrochloride per tablet.

C: Ephedrine/caffeine tablets 20/200 mg, DAK containing 20 mg of ephedrine hydrochloride and 200 mg of caffeine, the tablets were made according to Example 1B.

All tablets were identical with regard to weight, appearance and taste.

Study Plan

Drugs

One tablet was ingested at 8.30 a.m. with 150 ml water.

Food

The volunteers were allowed to eat a light breakfast not later than 7.00 a.m. on the day of study. The light breakfast consisted of 2 slices of white bread with butter and possibly jam, and juice, water or other caffeine-free beverages (except milk products). From 7.00 a.m. and until a light standardised lunch at 1.00 p.m. the volunteers were not allowed to eat. Drinking was allowed after 10.00 a.m. After lunch, the volunteers were allowed to eat and drink freely.

Restrictions

The volunteers were not allowed to ingest food or drinks with caffeine 3 days (72 hours) before the study and until the last blood sample was taken on the second day of study. Food or drinks with caffeine could be: Coffee, tea, cocoa, cola or other drinks with caffeine as well as any kind of chocolate products.

The volunteers were not allowed to drink alcohol 1 day (24 hours) before and during the sampling period.

The volunteers were not to change their smoking habits during the study period.

Other medications

No medication (except vitamins and minerals) were allowed 3 days before and during the study days.

Sampling

Blood sampling 16 blood samples were taken by vein puncture (Ven-Flon technique for the first 12 hours), before and at the following times after drug administration: 15, 30, 45, 60 minutes, 1.5, 2, 3, 4, 6, 8, 10, 12, 24, 28 and 32 hours.

The blood samples were allowed to stand 30 minutes protected from light, then centrifuged for 10 minutes at 3000 rpm. The serum was transferred to other vials and frozen until analysis.

Urine sampling

Urine was collected after ingestion of tablet B and tablet C, but not after tablet A.

Urine fractions were collected in brown glasses with wide necks just before and in the following intervals after drug administration: 0–3, 3–6, 6–9, 9–12, 12–24, 24–32 and 32–48 hours.

The urine samples were allowed to reach room temperature. The total volume and pH were measured within 24 hours from the sampling period and an aliquot of the sample was transferred to small vials and frozen until analysis.

Analysis of samples

Analysis of caffeine in serum

The concentration of caffeine and the metabolites theobromine, theophylline and paraxanthine in serum was determined by high pressure liquid chromatography (HPLC) according to a method described by Williams et al. (29), the method being slightly modified with regard to mobil phase, wave-length, extraction and guard column and, furthermore, no internal standard was included:

200 $\mu$l serum was acidified with 200 $\mu$l 0.1M hydrochloric acid and shaken with 5.0 ml 2-propanol: dichlormethane (1:9 v/v); 4 ml of the organic phase was transferred to a new vial after centrifugation and evaporated to dryness at 45° C. under nitrogen flow. The residue was re-dissolved in 200 $\mu$l sterile water and 50 $\mu$l were injected into the chromatographic system.

Chromatographic details

Columns: Lichrosorb RP8 (10 $\mu$m) (250 mm $\times$ 4.6 mm i.d.) equipped with a guard column (23 mm $\times$ 3.9 mm i.d.) containing Bondapak C-18/Corasil (37–50 $\mu$m).

Apparatus: Waters Assoc. Chromatography pump M 6000 A, Waters Assoc. Model 450 variable wavelength detector, UK 6 injector and Servogor Z 10 printer.

Mobil phase: Tetrahydrofurane-water (4.2:95.8 v/v).

Flow: 2 ml/min.

Wavelength: 270 nm.

Pressure: 3000 PSI.

Column temperature: 25° C.

AUFS: 0.01–0.02–0.04–0.1 at 10 mV.

Retention time: Theobromine 2.8 min., paraxanthine 3.6 min., theophylline 3.9 min., caffeine 5.2 min.

The content in the samples of caffeine, theophylline, paraxanthine and theobromine, respectively, was calculated from each person's own serum standard curve (0–1–5–10 $\mu$g/ml) after subtraction of the individual blank value.

The standard curves were linear in the range of 1–10 $\mu$g/ml and the recoveries in serum containing an added amount of a mixture of the 4 compounds were 83% (theobromine), 81% (paraxanthine), 90% (theophylline) and 99% (caffeine) compared to an aqueous solution containing all 4 compounds (0.2 $\mu$g/ml). The relative standard deviations in the actual range of measurement were 3.2% (theobromine), 4.9% (paraxanthine), 4.4% (theophylline) and 5.7% (caffeine). The detection limits were 0.04 $\mu$g/ml (theobromine), 0.06 $\mu$g/ml (theophylline and paraxanthine) and 0.08 $\mu$g/ml (caffeine).

The serum samples could be stored for at least 5 weeks in a freezer (−20° C.) without degradation.

Analysis of ephedrine in urine

The content of ephedrine and the metabolite norephedrine in urine was determined by high pressure liquid chromatography (HPLC) using a combination of the methods described by Lurie (30) and Lai et al. (31), slightly modified with regard to mobil phase, guard column and extraction method, and, furthermore, without internal standard:

2 ml urine was made alkaline with 0.5 ml 5% potassium hydroxide and shaken with 5 ml hexane: dichlormethane (60:40 v/v). After centrifugation, 3.5 ml of the organic phase was transferred to a new vial and shaken with 100 µl 0.1M hydrochloric acid and then evaporated to dryness at 40° C. under nitrogen flow. The residue was re-dissolved in 100 µl water and 50 µl were injected into the chromatographic system.

Chromatographic details

Columns: µBondapak C-18 (10 µm) (300 mm×3.9 mm i.d.) equipped with a guard column (23 mm×3.9 mm i.d.) containing Bondapak C18/Corasil (37–50 µm).

Apparatus: Waters Assoc. Chromatography pump Model 510, Waters Assoc. Model 440 Absorbance detectors, UK 6 injector and Servogor Z 10 printer.

Mobil phase: Methanol: 0.02M n-heptane sulphonic acid sodium salt: 1% acetic acid (35:64:1 v/v).

Flow: 2 ml/min.
Wavelength: 254 nm.
Pressure: 2500 PSI.
Column temperature: 40° C.
AUFS: 0.005–0.01–0.02–0.05–0.1 at 10 mV.
Retention time: Ephedrine 9.5 min., norephedrine 8.6 min.

The content in the samples of ephedrine and norephedrine was calculated from the individual urine standard curve (0.5–10–50 µg/ml) of each volunteer.

The standard curves were linear in the range of 0–50 µg/ml and the recoveries in urine containing an added amount of a mixture of the 2 compounds were 87% (ephedrine) and 36% (norephedrine) compared to an aqueous solution of the two compounds (50 µg/ml). The relative standard deviations in the actual range of measurement were 6.6% (ephedrine) and 7.7% (norephedrine). The detection limits were 0.3 µg/ml (ephedrine) and 0.6 µg/ml (norephedrine).

The urine samples could be stored for at least 3 weeks in a freezer (−20° C.) without any degradation.

Safety Evaluations

Blood pressure and heart rate were measured before and 2 and 4 hours after drug administration.

Adverse drug reactions were spontaneously reported by the volunteers. The symptom, time of onset, duration and severity (as mild, moderate or severe) of the event were recorded.

Kinetic Calculations

Caffeine and metabolites

The peak concentration ($C_{max}$) and the time to peak concentration ($T_{max}$) of caffeine and its metabolites, theobromine and paraxanthine were recorded. The total area under the serum concentration-time curve ($AUC_{0-\infty}$) was measured by the trapezoidal rule and extrapolated from $C_{32h}$ (the serum concentration at 32 h after administration) to infinity by $C_{32h}$ divided by $k_e$ (elimination rate constant). $AUC_{0-\infty}$ as well as the elimination half-life ($T_{\frac{1}{2}}$), mean residence time (MRT), absorption half-life of caffeine (($T_{\frac{1}{2}abs.}$), and metabolism half-life of paraxanthine ($T_{\frac{1}{2}met}$) were calculated by curve fitting with the simplex method (SIMPFIT) (32).

$AUC_{0-\infty}$ was furthermore corrected by $k_e$ to settle differences in elimination rate on the different treatment days.

Ephedrine and norephedrine

The actual amount of ephedrine and norephedrine excreted in urine in 48 hours ($Ae^{0-48}$) was calculated, as well as the maximum excretion rate ($\Delta Ae/\Delta t_{max}$) and the time to maximum excretion rate ($T_{max}^{\Delta Ae/\Delta t}$).

Statistical Analysis

Two-way analysis of variance was performed with SAS.GLM on all the kinetic parameters and the logarithmically transformed parameters. The same analysis on the cardiovascular data was performed on the difference (2-0 hours), (4-0 hours), and (4-2 hours) instead of the actual blood pressure and heart rate measurements.

Results

Caffeine and metabolites

Serum concentrations of caffeine, theobromine and paraxanthine (µg/ml) after administration of caffeine tablets 200 mg and ephedrine/caffeine tablets 20/200 mg, respectively, to 12 volunteers were measured. Another metabolite, theophylline was not detected (i.e. theophylline was not present or present in a concentration below the limit of detection, the limit being 0.06 µg/ml). The median values are shown in FIG. 4.

The pharmacokinetic parameters of caffeine, theobromine and paraxanthine calculated from the curves and by curve fitting are shown in Table 7 as mean and S.D. (Standard Deviation) is given, as well as the calculated p-values, two-way analysis of variance (SAS.GLM).

TABLE 7

Pharmacokinetic parameters after administration of caffeine tablets 200 mg and ephedrine/caffeine tablets 20/200 mg, respectively

| | Caffeine tablets 200 mg | | |
|---|---|---|---|
| | mean | S.D. | range |
| Caffeine | | | |
| $C_{max}$ (µg/ml) | 4.7 | 1.5 | 3.5–8.5 |
| $T_{max}$ (hours) | 1.1 | 0.8 | 0.25–3.0 |
| $AUC^{0-\infty}$ (µg/ml × hours) | 31.2 | 12.5 | 14.7–53.1 |
| $AUC^{0-\infty} \times K_e$ (µg/ml) | 5.4 | 1.6 | 3.5–9.6 |
| $t_{\frac{1}{2}}$ hours | 4.0 | 1.4 | 2.5–6.1 |
| $t_{\frac{1}{2}abs.}$ (hours) | 0.46 | 0.54 | 0.01–1.98 |
| MRT (hours) | 6.5 | 1.9 | 4.2–9.2 |
| Theobromine | | | |
| $C_{max}$ (µg/ml) | 0.28 | 0.12 | 0.11–0.51 |
| $T_{max}$ (hours) | 6.7 | 3.0 | 2.0–10.0 |
| $AUC^{0-32}$ (µg/ml × hours) | 4.1 | 2.9 | 0.5–9.7 |
| MRT (hours) | 9.9 | 3.4 | 5.4–15.6 |
| Paraxanthine | | | |
| $C_{max}$ (µg/ml) | 1.5 | 0.3 | 1.1–2.0 |
| $T_{max}$ (hours) | 6.4 | 2.1 | 3.0–10.0 |
| $AUC^{0-\infty}$ (µg/ml × hours) | 24.5 | 8.0 | 10.3–40.7 |
| $t_{\frac{1}{2}}$ (hours) | 6.6 | 4.2 | 2.2–15.5 |
| $t_{\frac{1}{2}met.}$ (hours) | 3.0 | 1.4 | 0.9–5.0 |
| MRT (hours) | 12.9 | 5.6 | 5.8–24.0 |

| | Ephedrine/caffeine tablets 20/200 mg[a] | | | |
|---|---|---|---|---|
| | mean | S.D. | range | p-value |
| Caffeine | | | | |
| $C_{max}$ (µg/ml) | 4.9 | 0.9 | 3.8–6.9 | |
| $T_{max}$ (hours) | 0.8 | 0.6 | 0.25–2.0 | |
| $AUC^{0-\infty}$ (µg/ml × hours) | 30.3 | 11.9 | 16.3–58.6 | |

TABLE 7-continued

Pharmacokinetic parameters after administration of caffeine tablets 200 mg and ephedrine/caffeine tablets 20/200 mg, respectively

| | | | |
|---|---|---|---|
| $AUC^{0-\infty} \times K_e$ (μg/ml) | 5.2 | 1.1 | 3.8–7.7 |
| $t_{\frac{1}{2}}$ hours | 4.0 | 0.8 | 2.8–5.3 |
| $t_{\frac{1}{2}abs.}$ (hours) | 0.41 | 0.55 | 0.01–2.00 |
| MRT (hours) | 6.3 | 1.5 | 4.5–9.5 |
| Theobromine | | | |
| $C_{max}$ (μg/ml) | 0.38 | 0.25 | 0.24–1.2 |
| $T_{max}$ (hours) | 8.4 | 5.6 | 1.0–24.0 |
| $AUC^{0-32}$ (μg/ml × hours) | 6.0 | 6.3 | 2.4–25.5 |
| MRT (hours) | 10.2 | 3.9 | 4.2–18.8 |
| Paraxanthine | | | |
| $C_{max}$ (μg/ml) | 1.6 | 0.2 | 1.3–2.0 |
| $T_{max}$ (hours) | 4.8 | 1.5 | 3.0–8.0 |
| $AUC^{0-\infty}$ (μg/ml × hours) | 24.1 | 8.0 | 15.2–40.2 |
| $t_{\frac{1}{2}}$ (hours) | 6.1 | 3.4 | 2.8–14.9 |
| $t_{\frac{1}{2}met.}$ (hours) | 2.4 | 1.1 | 0.7–4.0 |
| MRT (hours) | 11.8 | 4.6 | 7.8–21.9 |

[a)] 20 mg ephedrine hydrochloride and 200 mg caffeine

Only $T_{max}$ of paraxanthine after administration of the two tablet preparations (caffeine tablets 200 mg and ephedrine/caffeine tablets 20/200 mg) shows a significant difference, all the other parameters were non-significant (p>0.05).

Ephedrine and norephedrine

The amount of ephedrine and the metabolite norephedrine (mg) excreted in the urine during suitable sampling intervals and the total amount (mg) excreted in 48 hours after administration of ephedrine tablets 20 mg and ephedrine/caffeine tablets 20/200 mg to 12 volunteers were measured as well as the urine volumes excreted in the sampling intervals. Furthermore, the pH of the urine samples were determined.

FIG. 4 shows the median curve of the excretion rate of ephedrine.

TABLE 8

Pharmacokinetic parameters after administration of ephedrine tablets 20 mg and ephedrine/caffeine tablets 20/200 mg, respectively

| | Ephedrine tablets 20 mg[a)] | | |
|---|---|---|---|
| | mean | S.D. | range |
| Ephedrine | | | |
| $Ae^{0-48}$ (mg) | 13.8 | 2.5 | 10.3–19.5 |
| $\Delta Ae/\Delta t_{max}$ (mg/hours) | 1.03 | 0.26 | 0.63–1.48 |
| $T_{max}^{\Delta A2/\Delta t}$ (hours) | 4.0 | 2.5 | 1.5–7.5 |
| Norephedrine | | | |
| $Ae^{0-48}$ (mg) | 4.2 | 3.6 | nd–11.2 |
| $\Delta Ae/\Delta t_{max}$ (mg/hours) | 0.33 | 0.29 | nd–0.94 |
| $T_{max}^{\Delta A2/\Delta t}$ (hours) | 3.1 | 3.3 | 1.5–7.5 |

| | Ephedrine/caffeine tablets 20/200 mg | | | |
|---|---|---|---|---|
| | x̄ | S.D. | range | p-value |
| Ephedrine | | | | |
| $Ae^{0-48}$ (mg) | 13.8 | 3.8 | 8.8–22.0 | 0.99 |
| $\Delta Ae/\Delta t_{max}$ (mg/hours) | 1.09 | 0.32 | 0.72–1.81 | 0.65 |
| $T_{max}^{\Delta A2/\Delta t}$ (hours) | 2.8 | 2.4 | 1.5–7.5 | 0.26 |
| Norephedrine | | | | |
| $Ae^{0-48}$ (mg) | 3.0 | 3.1 | nd–10.6 | 0.50 |
| $\Delta Ae/\Delta t_{max}$ (mg/hours) | 0.17 | 0.14 | nd–0.43 | 0.015 |
| $T_{max}^{\Delta A2/\Delta t}$ (hours) | 2.9 | 5.2 | nd–18.0 | 0.92 | nd = not detectable
[a)] containing 20 mg ephedrine hydrochloride

In Table 8 is shown the calculated parameters $Ae^{0-48}$, $\Delta Ae/\Delta t_{max}$ and $T_{max}^{\Delta Ae/\Delta t}$ for ephedrine and norephedrine with mean, S.D., median and range as well as the obtained p-values, two-way analysis of variance (SAS.GLM)

Only $\Delta Ae/\Delta t_{max}$ of norephedrine was significant, the other parameters were non-significant (p>0.05)

Thus, the study did not show any significant difference in the absorption (i.e. in the amount absorbed or in the rate of absorption) of caffeine from Caffeine tablets 200 mg and Ephedrine/Caffeine tablets 20/200 mg and in the absorption of ephedrine from Ephedrine tablets 20 mg and Ephedrine/Caffeine tablets 20/200 mg. In other words, no pharmacokinetic interaction between ephedrine and caffeine was found. Thus, the supra-additive effect observed after oral administration of a composition of a combination of ephedrine and caffeine comprising 20 mg ephedrine hydrochloride and 200 mg caffeine (see Example 2) is indeed a supra-additive effect and is not due to a change in the pharmacokinetics of ephedrine and caffeine after administration of the combination tablet.

Furthermore, no clinically important pharmacokinetic interactions between caffeine and ephedrine or their metabolites were observed, and consequently no accumulation of toxic metabolites will take place after administration of the combination tablet comprising ephedrine and caffeine.

EXAMPLE 5

Double blind, controlled study of the weight reducing effect and safety in obese patients of ephedrine/caffeine combination tablets (EFK) compared with ephedrine, caffeine and placebo tablets The study was carried out at Hvidovre Hospital University of Copenhagen, Denmark.

Aim

The aim of the investigation was 1) to study the weight reducing effect and safety of ephedrine/caffeine combination tablets (EFK), compared to ephedrine, caffeine and placebo tablets in obese patients, and 2) to investigate whether the combination of ephedrine and caffeine possessed a supra-additive effect on weight loss.

Study Design

The study was designed as a double blind, randomised, parallel study with 4 treatment groups in a 2×2 factorial design.

All patients were treated with the trial medication and prescribed a 4.2 MJ/day diet for 24 weeks.

Patient Selection

Included were 180 patients between 20 and 65 years of age and with 20% to 80% overweight, who had given their informed consent.

Excluded were:

1) Patients with hypertension (diastolic blood pressure more than 110 mmHg) and/or receiving antihypertensive treatment other than diuretics, 2) pregnant or lactating women, or women who wished to become pregnant,
3) patients with different diseases that could interact with the trial medication or in cases where trial medication could be a potential risk to the health of the patient, e.g. patients with gastrointestinal diseases which could delay drug absorption; heart diseases, such as arrhythmia, the WPW syndrome and uncompensated heart diseases; treatment-demanding serious endocrinological diseases (type I diabetes); or diseases of the thyroid gland,
4) patients with malignant diseases within the previous 5 years (except carcinoma basocellulare), psychoses, drug addictions,
5) patients who within 14 days before entering the trial were treated with drugs known to promote overweight, or treated with monoamine oxidase inhibitors,
6) patients who had surgical treatment for their overweight, apart from cosmetic surgery,
7) patients who had changed oral contraceptives during the last 3 months before or who were treated with theophylline or other methylxanthines during the last month before entering the trial,
8) patient with abnormal laboratory results at the time of entry which might indicate that participation could be injurious to their health, and
9) patients who had initiated slimming treatment and lost more than 8 kg during the last two months before start of the trial.

Increased levels of serum triglyceride acids and serum cholesterol, however, did not exclude the patients.

141 patients completed the study: 35 in the EFK (combination of ephedrine and caffeine), ephedrine and placebo groups and 36 in the caffeine group. 39 patients were withdrawn during the study, 6 of these due to adverse drug reactions: 3 from the EFK group, 1 from the ephedrine group and 2 from the caffeine group. In all cases it was recorded whether the withdrawals or dropouts were due to treatment failure, adverse drug reactions, abnormal laboratory values, complication of the disease, pregnancy, non-compliance, unwillingness to participate in the trial or other. If patients were withdrawn due to adverse drug reactions, abnormal laboratory values, abnormal blood pressure or ECG changes, they were observed until the symptoms had disappeared and then contacted at monthly intervals for at least 3 months.

Treatment administered
A. EFK group: EFK tablets containing a combination of 20 mg ephedrine hydrochloride and 200 mg caffeine prepared according to Example 1B.
B. Ephedrine group: Ephedrine tablets containing 20 mg ephedrine hydrochloride.
C. Caffeine group: Caffeine tablets containing 200 mg caffeine.
D. Placebo group: Placebo tablets without active drug substances.

The tablets were identical with regard to weight, appearance, and taste.

The patients were prescribed 1 tablet 3 times daily one hour before meals together with a 4.2 MJ/day diet consisting of NUPO ® protein nutrition powder (33) (1.6 MJ/day) and free additional choice of food (2.6 MJ/day) for 24 weeks.

During the study, no other treatment for overweight or obesity was allowed. Only treatment which did not interact with the study medication was allowed after consultation with the physician. Compliance was checked by counting the returned tablets.

Study Plan

Before entering the study, patients were informed about the study, their initial clinical condition was examined and their voluntary informed consent to participate in the study was obtained.

The patients's age, height, weight, and sex were recorded along with concomitant medication and caffeine consumption, and the patients received diet instructions.

At every two weeks, the patients received diet instruction and were weighed by dietitians. If the patient did not comply with the NUPO ® diet, it was changed to a NUPO ®-free diet of 4.2 MJ/day.

Every four weeks the patients were also examined by a physician.

By randomization the patients were assigned to the 4 treatment groups (EFK, ephedrine, caffeine and placebo, respectively). The sex distribution in the 4 groups was not statistically different ($p=0.09$). The average age of the patients were 36 years, average height 167 cm, average weight 95 kg, and the average % overweight was 51%. The 4 groups were comparable with respect to age ($p=0.59$), height ($p=0.48$), weight ($p=0.68$), and % overweight ($p=0.79$). The average initial systolic blood pressure was 126 mmHg, the average initial diastolic blood pressure was 81 mmHg and the average initial heart rate (heart rate) was 77 BPM (beats per minute). The 4 groups were comparable with regard to both initial systolic blood pressure ($p=0.36$), initial diastolic blood pressure ($p=0.38$) and initial heart rate ($p=0.32$). The 4 groups were also comparable with regard to initial caffeine consumption, with an average of 5.8 arbitrary cups of coffee per day ($p=0.20$).

Effect evaluation
Body weight

The patients were weighed on a decimal scale by dietitians at each visit. A Seca electronic scale (model 707) was used. The weighing limit was 200 kg, with 100 g graduations. The scale was calibrated every week.

Safety evaluation
Subjective methods

Adverse drug reactions were recorded by the investigators at each visit by indirect questioning and/or by spontaneous reporting by the patient.

14 days after discontinuation of the treatment, a psychiatrist recorded any inconveniences the patient might have had during this period and physical and psychological symptoms were registered.

Objective methods
General physical examination

Before entering the trial, the investigator carried out a general physical examination on all patients.

Blood pressure and heart rate measurements

Blood pressure was measured with a Trimline Sphygmomanometer (PyMaH) by the investigator every 4 weeks. After at least 10 minutes rest, the measurements were carried out in the right arm of the patient a.m. Riva-Rocci with the patient being positioned in a sitting position. A cuff of 14 to 16 cm width was employed. The manometer pressure was slowly and gradually reduced from 200 mmHg and the first Korotkoff sound was registered as the systolic blood pressure. The diastolic blood pressure was determined at the manometer pressure when the Korotkoff sound quality changes from tapping to muffled.

The heart rate was determined by palpation of the peripheral heart rate in the right radial artery.

ECG

A 9-lead EGG was taken before entry in the trial and after 12 and 24 weeks of treatment. Two EGG apparatuses (Minigraf 3 minor, Mass., U.S.A. and MAC 1, Marquette Electronics Inc., U.S.A.) were used during the study. Conveying speed was 25 mm/min.

Laboratory methods

Blood and urine samples for laboratory tests were taken before entry, and after 12 and 24 weeks.

The following tests were carried out:

Haematology parameters: Haemoglobin, white blood cell count and platelets were analyzed and differential leucocyte was counted.

Plasma protein parameters: Albumin was analyzed.

Acid-alkaline balance parameters: Total bicarbonate was analyzed.

Electrolyte parameters: Sodium and potassium were analyzed.

Liver parameters: Bilirubin, alkaline phosphates, lactate dehydrogenase (LDH) and aspartate aminotransferase (ASAT) were analyzed in order to control liver function.

Kidney parameters: Creatinine and uric acid were analyzed. Urine was examined for glucose, haemoglobin and protein by a qualitative stick test.

Metabolic factors: In order to evaluate changes in the glucose and lipid metabolism of the patients during the study, triglyceride acid (TGA), cholesterol and fasting glucose were analyzed.

All clinical-chemical analyses apart from TGA and test strips for urine, were carried out at Department of Clinical Chemistry, Hvidovre Hospital, in accordance with their routine methods and assays, including the department's running quality control. The methods and the assays are routine procedures and are well-documented (7,40–48). TGA was analyzed and test strips for urine assessed at the Department of Internal Medicine, Division of Endocrinology, Hvidovre Hospital's own laboratory following the same routine procedures as above (26).

Statistical methods

The statistical analysis of weight loss was based on the logarithm of the initial body weight minus logarithm of the body weight at the actual visit. This was done due to a skewness in data caused by the patients with the highest initial body weight having the highest weight loss.

For the statistical analysis, students one-sample t-test SAS.GLM was used.

The correlations between body weight and triglyceride acid, cholesterol and fasting glucose were performed by analysis of variance (SAS.GLM).

The supra-additive effect was expressed by the effect of ephedrine in the presence of caffeine minus the effect of ephedrine in the absence of caffeine, i.e. the supra-additive effect was the effect of EFK minus the effect of ephedrine, minus the effect of caffeine, plus the effect of placebo. As the data was logarithmically transformed as expressed above, a negative value corresponds to a supra-additive effect. Nil corresponds to additive effect and a positive value corresponds to a sub-additive effect.

The statistical analysis was performed by a one-way analysis of variance (SAS.GLM).

Demographic data were expressed by the mean value for each of the 4 treatment groups and compared by one-way analysis of variance (SAS.GLM). The initial number of patients (males and females) in each group was compared by a Chi$^2$-test (SAS PROC FREQ).

The mean difference of blood pressure, heart rate and laboratory data from the initial values (week 0) at week 12 and at week 24 was compared to initial values for each treatment group by Students' one sample t-test (SAS). Comparison of the treatment groups at a particular visit was done by one-way analysis of variance (SAS.GLM). The difference from initial values was used in order to prevent chance events influencing the results. Patients with high values, for instance, who dropped out would thus influence the mean value at the next control, without a real difference being present.

Results

Weight loss

One patient from the caffeine treatment group had a strongly deviant course of weight loss compared to the rest of the patients. He lost 42.6 kg compared to an average of 11.7 kg for the whole group during the 24 weeks. The results from this patient were therefore excluded from the analysis and the analysis was carried out on 140 patients (118 women and 22 men).

Figure 5:
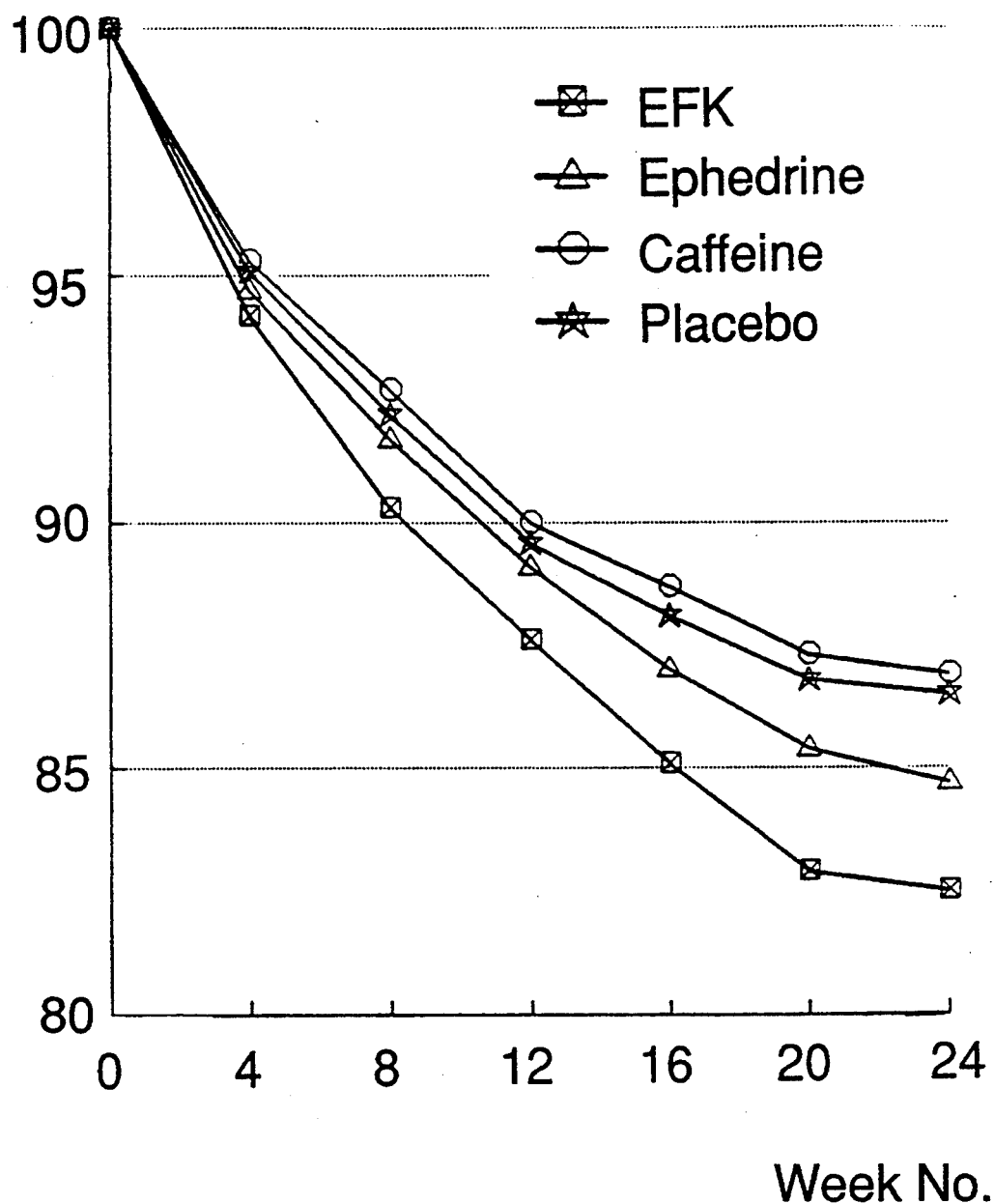
FIG. 5: Changes in body weight given as percentages of initial weight during 24 weeks of treatment with EFK tablets, ephedrine tablets 20 mg, caffeine tablets 200 mg and placebo, respectively. For details see Example 5.

The patients had a significant weight loss in all 4 treatment groups after 4 weeks of treatment and during the rest of the study. The patients treated with EFK had a significantly larger weight loss compared to placebo after 8 weeks of treatment (FIG. 5).

After 24 weeks of treatment the relative body weight (i.e.

$$\frac{\text{body weight after 24 weeks of treatment}}{\text{body weight before treatment}} \times 100\%)$$

was 82.5% in the EFK group, 84.7% in the ephedrine group, 87.6% in the caffeine group and 86.5% in the placebo group as seen in the following Table 9.

TABLE 9

| Week No. | Treatment group | | | |
|---|---|---|---|---|
| | EFK | Ephedrine | Caffeine | Placebo |
| 0 | 100.0 | 100.0 | 100.0 | 100.0 |
| 4 | 94.2 | 94.7 | 95.5 | 95.1 |
| 8 | 90.3 | 91.7 | 93.0 | 92.2 |
| 12 | 87.6 | 89.1 | 90.4 | 89.6 |
| 16 | 85.1 | 87.0 | 89.3 | 88.1 |
| 20 | 82.9 | 85.4 | 88.0 | 86.8 |
| 24 | 82.5 | 84.7 | 87.6 | 86.5 |

Relative body weight in the 4 treatment groups during the study

| Week No. | Treatment Group | |
|---|---|---|
| | EFK/placebo[a] | Supra-additive effect[a],[b] |
| | p | p |
| 0 | | |
| 4 | 0.11 | 0.18 |
| 8 | 0.03 | 0.04 |
| 12 | 0.05 | 0.10 |
| 16 | 0.03 | 0.06 |
| 20 | 0.008 | 0.04 |
| 24 | 0.02 | 0.09 |

[a]Difference between groups. One way analysis of variance. (SAS.GLM), significance value p is given
[b]EFK versus both ephedrine and caffeine Compared with the predicted weight loss after separate administration of ephedrine and caffeine, an unexpected additional weight loss of 3.5 kg was found after EFK administration.

In conclusion, EFK had a significant better weight reducing effect than placebo, and EFK showed significant supra-additive effect compared to the predictive, theoretically estimated effects of combinations of ephedrine and caffeine, the calculation being based on the data in Table 9 for separate administration of the two drugs at different times, i.e. the separate dose responses were added after subtracting the average placebo responses.

Safety evaluation 39 patients were withdrawn during the study, 6 of these were withdrawn due to adverse reactions. 74 patients complained of adverse drug reactions: 27 in the EFK group, 20 in the ephedrine group, 16 in the caffeine group and 11 in the placebo group. The most frequently reported symptoms from the active treatment groups were CNS symptoms, such as insomnia, tremor and dizziness. Tachycardia, palpitations, postural hypotension and hypertension were also reported. Most of the adverse drug reaction were reported in the beginning of the study and they were generally of short duration. There were no physical or psychological abstinence symptoms after 24 weeks of treatment. Some of the patients, however, complained of inconveniences after drug withdrawal. 34 patient complained of hunger, especially those who had been treated with ephedrine. Headache was reported by 27 patients, especially patients from the caffeine group. Finally, significantly more patients from the EFK group complained of tiredness after drug withdrawal.

Thus, no serious side effects of any of the treatments have been observed.

Blood pressure and heart rate measurements

Figure 6:
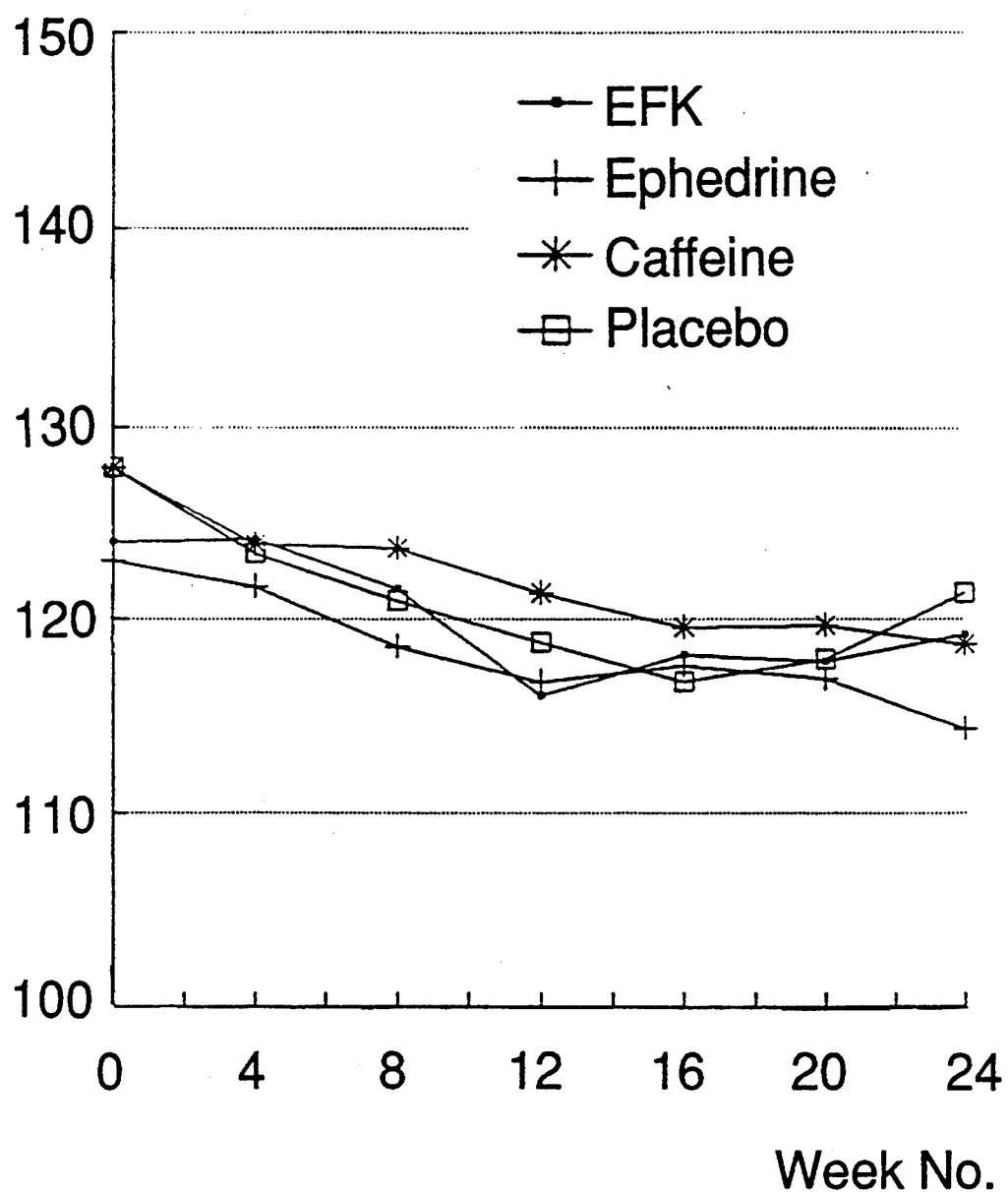
FIG. 6: Changes in systolic blood pressure during 24 weeks of treatment with EFK tablets, ephedrine tablets 20 mg, caffeine tablets 200 mg and placebo, respectively. For details see Example 5.
Figure 7:
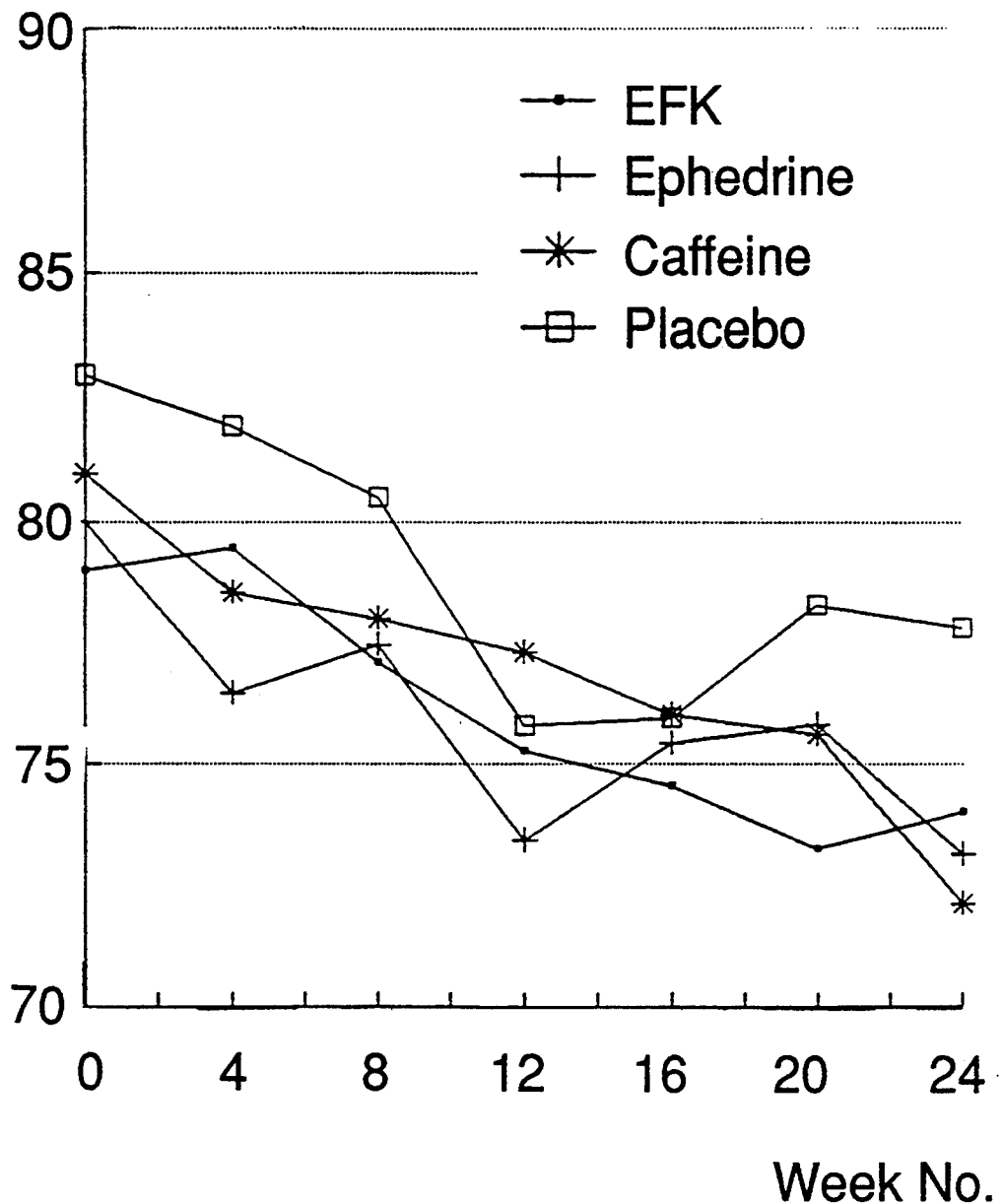
FIG. 7: Changes in diastolic blood pressure during 24 weeks of treatment with EFK tablets, ephedrine tablets 20 mg, caffeine tablets 200 mg and placebo, respectively. For details see Example 5.

Both systolic and diastolic blood pressure decreased during the study period in all 4 treatment groups (FIG. 6 and FIG. 7).

At week 24, average systolic blood pressure decreased 4.8 mmHg in the EFK group (4.0% of initial value), 8.7 mmHg in the ephedrine group (7.0% of initial value), 9.3 mmHg in the caffeine group (7.3% of initial value) and 6.7 mmHg in the placebo group (5.2% of the initial value). There were no statistically significant differences between the groups (p=0.42), but the decreases within the group were significant after 12 weeks.

At week 24, average diastolic blood pressure decreased 5.0 mmHg in the EFK group (6.3% of initial value), 6.9 mmHg in the ephedrine group (8.6% of initial value), 8.9 mmHg in the caffeine group (11.0% of initial value) and 5.2 mmHg in the placebo group (6.3% of initial value). Similar to the results of the part of the study concerning systolic blood pressure, no statistically significant differences of the average diastolic blood pressure between the groups (p=0.36) were observed, but the decreases of the average diastolic blood pressure within the groups were significant after 12 weeks (the p value is between 0.0001 and 0.01). The decrease in diastolic blood pressure was correlated to the weight loss being calculated for all patients both after 12 and 24 weeks (p=0.01 and 0.03, respectively).

Concerning blood pressure it can thus be concluded that administration of EFK in combination with a diet resulted in a significant decrease in both systolic and diastolic blood pressure.

Figure 8:
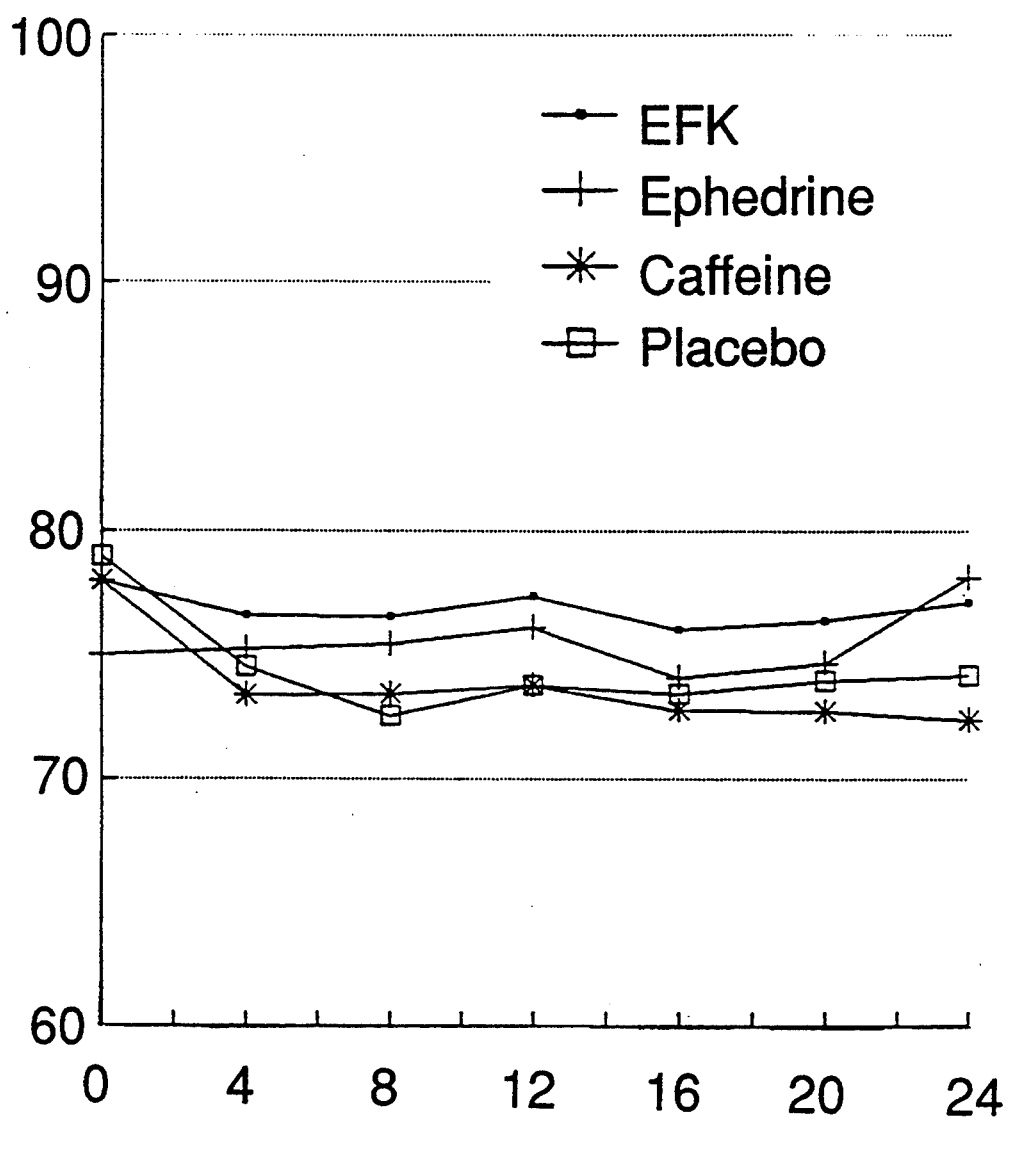
FIG. 8: Changes in heart rate during 24 weeks of treatment with EFK tablets, ephedrine tablets 20 mg, caffeine tablets 200 mg and placebo, respectively. For details see Example 5.

At week 24, average heart rate decreased 0.9 BPM in the EFK group (1.2% of initial value) −3.1 BPM (i.e. an increase) in the ephedrine group (−4.3% of initial value), 5.7 BPM in the caffeine group (7.3% of initial value) and 4.9 BPM in the placebo group (6.2% of initial value). As seen from FIG. 8, especially the heart rate for the EFK and ephedrine group fluctuates during the treatment period. The differences between the 4 treatment groups were statistically significant after 12 and 24 weeks of treatment with p-values of 0.03 and 0.003, respectively. In addition, correlation of the decrease in heart rate to the weight loss at week 12 and 24 was significant (p=0.04 and 0.008, respectively).

Thus, it can be concluded that treatment with EFK in combination with a diet significantly decreases the heart rate.

Laboratory Methods

Clinically influential changes were only observed in the values concerning serum triglyceride acid and fasting serum glucose. Statistically significant decreases in triglycerides and fasting glucose were observed in all 4 treatment groups. This will be seen from the following Tables 10 and 11.

TABLE 10

Mean difference in fasting serum glucose in the 4 treatment groups during the 24 weeks study

| Week | EFK | Ephedrine | Caffeine | Placebo |
|---|---|---|---|---|
| 0[a] | 4.98 | 5.34 | 5.21 | 5.16 |
| 12[b] | −0.10 | −0.55 | −0.18 | −0.29 |
| 12 | (0.28) | (0.001) | (0.11) | (0.008) |
| 24[b] | −0.37 | −0.46 | −0.42 | −0.35 |
| 24 | (0.0001) | (0.002) | (0.0006) | (0.002) |

[a] initial values are given (reference values 4.2–6.2 mmol/l)
[b] difference from initial values.

The values in parenthesis are significance values, p. Students one-sample t-test (SAS Univariate)

TABLE 11

Mean difference in serum triglycerides in the 4 treatment groups during the 24 weeks study

| Week | EFK | Ephedrine | Caffeine | Placebo |
|---|---|---|---|---|
| 0[a] | 1.68 | 1.56 | 1.51 | 1.95 |
| 12 | −0.29 | −0.14 | −0.11 | −0.37 |
| p[b] | (0.02) | (0.08) | (0.16) | (0.004) |
| 24 | −0.57 | −0.66 | −0.32 | −0.86 |
| p[b] | (0.001) | (0.004) | (0.002) | (0.01) |

[a] initial values are given (reference values 0.09–1.41 mmol/l)
[b] difference from initial values.

The values in parenthesis are significance values, p. Students one-sample t-test (SAS Univariate)

Furthermore, the decrease in serum triglyceride acid was significantly correlated to weight loss, the p-values being 0.07, 0.2, 0.002 and 0.0001 for the EFK, ephedrine, caffeine and placebo group, respectively.

To sum up, the described clinical controlled study after 24 weeks of treatment has shown that:
1. EFK is effective in the treatment of obesity, the treatment being combined with a 4.2 MJ/day diet,
2. EFK has a supra-additive body weight reducing effect,
3. treatment with EFK results in a decrease in blood pressure (both systolic and diastolic blood pressure) and in heart rate,
4. treatment with EFK results in a significant decrease in the values of fasting serum glucose and serum triglycerides,
5. treatment with EFK affords no serious side effects and no abstinence symptoms after withdrawal.

EXAMPLE 6

An open evaluation of the long term efficacy and safety of an ephedrine/caffeine combination tablet (EFK) in the treatment of overweight and obesity.

The study was carried out at Hvidovre Hospital, University of Copenhagen, Denmark Aim The purpose of the study was to investigate 1) the long term adverse reaction profile of the EFK tablets, and 2) the long term efficacy of the EFK tablets after 24 weeks of treatment of overweight or obesity with a 5.04 MJ/day diet.

Study Design

The study was designed as an open study. All patients were treated with EFK tablets and prescribed a 5.04 MJ/day diet for 24 weeks.

Patient Selection

Included in the study were patients who had completed the 24 weeks study described in Example 5 without adverse drug reactions and who, furthermore, had been without treatment for 2 weeks. In addition, the patients were more than 10% overweight at the start of the present study.

Thus, 128 patients entered the follow-up study: 30 from the EFK group, 31 from the ephedrine group, 35 from the caffeine group and 32 from the placebo group.

101 patients (85 women and 16 men) completed the whole study period of 50 weeks. 27 patients were withdrawn or dropped out during the study: 6 patients from the EFK group, 7 from each of the other groups.

In all cases it was recorded whether the withdrawal was due to treatment failure, adverse drug reactions, abnormal laboratory values, complication of the disease, pregnancy, non-compliance, unwillingness to participate in the trial or other reasons. It was also recorded if a patient was withdrawn as a consequence of having reached the ideal weight. If patients were withdrawn due to adverse drug reactions or abnormal laboratory results, they were observed until the symptoms had disappeared and then they were contacted monthly for at least 3 months.

Excluded were:
1) Patients with hypertension (diastolic blood pressure more than 110 mmHg) and/or receiving antihypertensive treatment other than diuretics,
2) pregnant or lactating women, or women who wished to become pregnant,
3) patients with different diseases that could interact with the trial medication or in cases where trial medication could be a potential risk to the health of the patient, e.g. patients with gastrointestinal diseases which could delay drug absorption; heart diseases, such as arrhythmia, the WPW syndrome and uncompensated heart diseases; treatment-demanding serious endocrinological diseases (type I diabetes); or diseases of the thyroid gland,
4) patients with malignant diseases within the previous 5 years (except carcinoma basocellulare), psychoses, drug addiction or dependence,
5) patients who within 14 days before entering the trial were treated with drugs known to promote overweight, anorectic drugs other than EFK, ephedrine or caffeine, or treated with monoamine oxidase inhibitors,
6) patients who had changed oral contraceptives during the last 3 months before the study, or who were treated with theophylline or other methylxanthines during the last month before entering the study,
7) patients who had surgical treatment for their obesity, apart from cosmetic surgery,
8) patients with abnormal laboratory results at the time of entry, the results indicating that participation in the study could be injurious to their health.

Increased levels of serum triglyceride acids and serum cholesterol, however, did not exclude the patients.

Treatment administered

EFK tablets containing ephedrine hydrochloride 20 mg, and caffeine 200 mg were prepared according to Example 1C.

The patients followed a 5.04 MJ/day diet (34) and were prescribed 1 tablet 3 times daily one hour before meals.

During the study, no other treatment for overweight or obesity was allowed. Only treatment that does not interact with the study medication was allowed after consultation with the physician.

Compliance was checked by counting the returned tablets.

Study Plan

Before entering the study, the patients were informed about the study and their eligibility was evaluated on the basis of inclusion and exclusion criteria. The patients' voluntary, informed consent was obtained and the body weight of the patients was recorded.

The patients should start medication within 28 days after completion of the study described in Example 5. From Example 5 the patients' age, sex and weight along with concomitant medication and total caffeine consumption were known and the parameters used as pre-study evaluation in this study.

Every 4 weeks, the patients attended dietitians. The count of the week numbers was continued from the study described in Example 5; the visits in this study being at week 26, 30, 34, 38, 42, 46 and 50. At these visits, they received diet instructions, had their weight recorded and the were questioned about adverse drug reactions.

If the patients reached their ideal body weight during the study, the drug therapy ceased, but they could still attend the dietitians.

At week 38 and 50, the blood pressure and heart rate were measured by a physician and adverse drug reactions and change in concomitant therapy was noted.

ECG and blood samples for laboratory tests were taken at week 50.

Effect Evaluation

Body weight

The patients were weighed on a decimal scale by dietitians at each visit. A Seca electronic scale was used (model 707). The weighing upper limit was 200 kg, with 100 g graduations. The scale was calibrated every week.

Safety Evaluation

Subjective methods

Adverse drug reactions were recorded by the investigators at each visit by indirect questioning and/or by spontaneous reporting by the patient.

Objective Methods

Blood pressure and heart rate measurements

Blood pressure was measured with a Trimline sphygmomanometer (PyMaH) by the investigator at week 38 and 50. After at least 10 minutes rest, the measurements were carried out in the right arm a.m. Riva-Rocci with the patient being positioned in a sitting position. A cuff of 14 to 16 cm with was employed. The manometer pressure was slowly and gradually reduced from 200 mmHg and the first Korotkoff sound was registered as the systolic blood pressure. The diastolic blood pressure was determined at the manometer pressure when the Korotkoff sound quality changes from tapping to muffled.

The heart rate was determined by palpation of the peripheral heart rate in the right radial artery, also at week 38 and 50.

ECG

A 9-lead ECG was taken at week 50 (see Example 5 for details).

Laboratory Methods

Blood and urine samples for laboratory tests were taken at week 50. The same test as described according to Example 5 were carried out.

Statistical Methods

In order to examine whether the medication given in the study described in Example 5 (i.e. EFK, ephedrine, caffeine and placebo) had any influence on the results from the present study, both with regard to efficacy and safety, the data were analyzed with respect to the previous drug treatment (i.e. the patients were still allocated to the four treatment groups from Example 5).

The statistical analysis of weight data was performed corresponding to the statistical analysis described in Example 5, the analysis being performed on the results given as the difference from baseline (week 26), the results being obtained at each of the 4-week visits.

The mean difference of blood pressure and heart rate from baseline (week 0) at week 38 and at week 50, respectively, and from week 24 to week 50 was compared to baseline values for each treatment group by Students' one sample t-test (SAS Univariate). Comparison of the treatment groups at a particular visit was done by one-way analysis of variance (SAS.GLM).

The analysis of the laboratory data were based on the difference from baseline (week 0) to week 50.

The difference from baseline was used in order to prevent stochastic variations influencing the result. If the results given as the difference from baseline was not used, patients with high values who e.g. later dropped out of the study could influence the mean value at the next control, without a real difference being present and thus, biassing the results. The number of patients with specific characteristics was used for all other surveys and analyzed by the Chi$^2$-test (SAS PROC FREQ), Results Weight loss The patients in this study were all treated with EFK and they had an additional weight loss, although the weight loss during the 24 weeks of the present study statistically was significantly lower than in the study from Example 5. However, it should be considered that in the present study, a diet of 5.04 MJ/day is taken in comparison of a diet of 4.2 MJ/day in the former study from Example 5. Furthermore, only patients with more than 10% overweight at the end of the study described in Example 5 were included. Thus, not all patients originally included at week 0 participated in this study starting at week 26.

At week 26, the mean body weight for the whole patient population was 83.9 kg. The reduction of the weight continued during this follow-up study with an average weight loss of 2.2 kg (p=0.0001) at week 50. The body weight was significantly lower during the whole study compared to the week 26 body weight.

Comparing the weight loss in the 4 previous treatment groups (Example 5), noticing that all treatment groups from week 26 were treated with EFK tablets, the average weight loss was 1.6 kg (p=0.12) in the EFK group, 0.8 kg (p=0.33) in the ephedrine group, 3.1 kg (p=0.001) in the caffeine group and 3.3 kg (p=0.003) in the placebo group. Thus, the patients who had been treated with caffeine or placebo in the study from Example 5 had an additional weight loss during this study, whereas the patients from the EFK and ephedrine groups only had minor weight reduction. There was no difference between the groups after 50 weeks of treatment.

Figure 9:
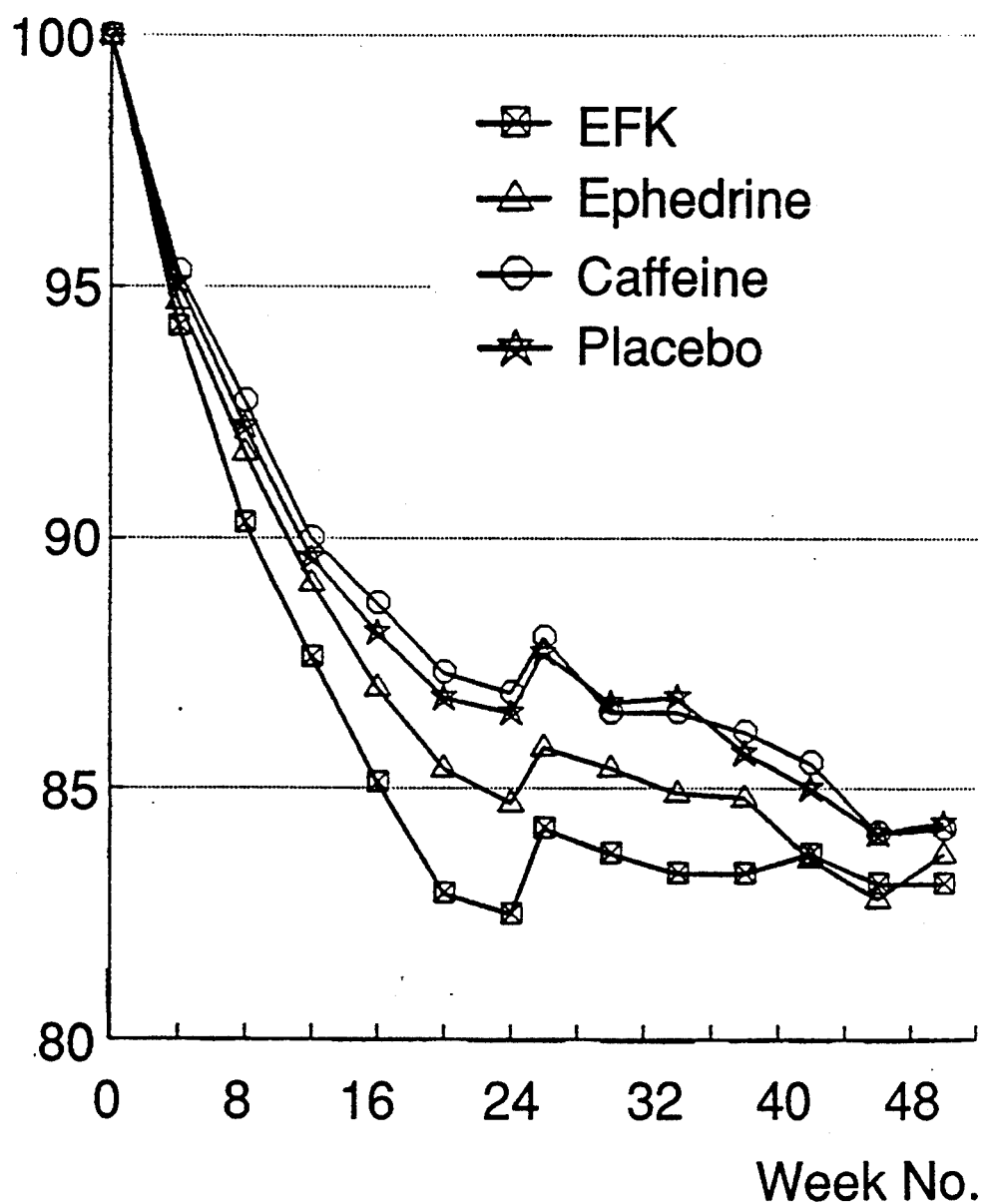
FIG. 9: During 24 weeks of treatment with EFK tablets, ephedrine tablets 20 mg, caffeine tablets 200 mg and placebo, respectively, followed by treatment with EFK tablets in all four groups, changes in body weight are given as percentages of initial weight. For details see Example 5.
Figure 10:
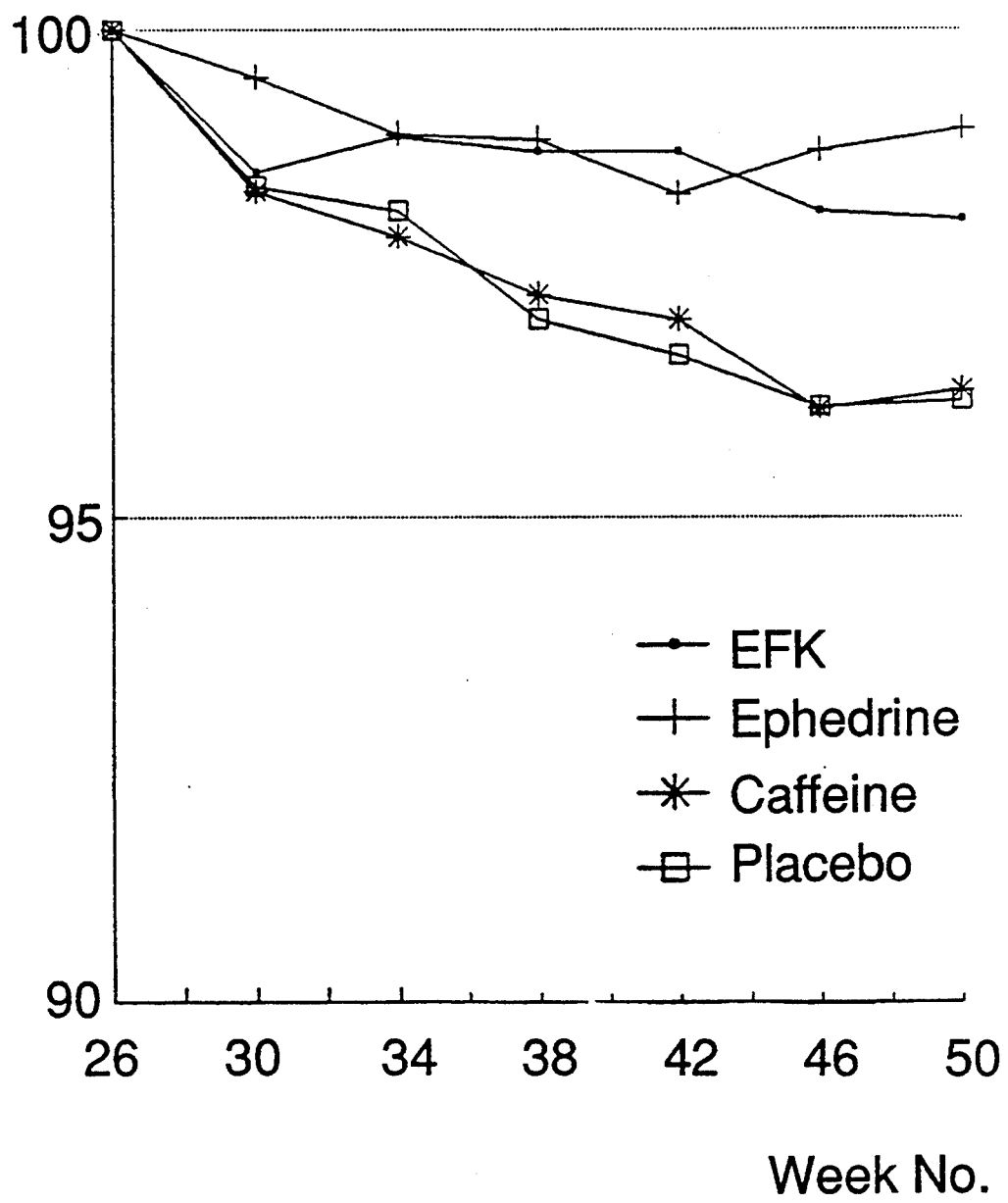
FIG. 10: Changes in body weight given as percentages of weight of week 26. For details see Example 6.

The relative percentage of body weights with baseline values from week 0 (i.e. the start of the study from Example 5) and week 26 (i.e. the start of the present study) are shown in FIGS. 9 and 10, respectively. Due to the courses of the curves it seems reasonable to maintain the allocation of patients to the 4 treatment groups from Example 5.

In conclusion, all patients had additional weight reduction. The largest effect was observed on previously untreated or caffeine treated patients (placebo or caffeine groups, respectively) showing a superior effect of EFK with respect to placebo and caffeine.

Safety Evaluation 27 patients were withdrawn or dropped out during the study, 4 of these due to adverse reactions (2 from the caffeine and ephedrine groups), 2 with tachycardia, 1 with depression, nervousness and irritability and 1 with increased sweating, dysaesthesia of the fingers and sleepiness. The other 23 patients were withdrawn or dropped out due to other reasons as e.g. non-compliance, unwillingness to continuation, pregnancy or various complications (e.g. infectious diseases).

80% of the patients complained of adverse drug reactions. These were primarily related to the central nerve and cardiovascular system. The majority of the adverse reactions were mild and short-lasting and most of them (75%) occurred in the beginning of the study.

Thus, no serious side effects of the EFK treatment have been observed.

Objective Methods

Blood pressure and heart rate measurements

Both systolic and diastolic blood pressure decreased during the study period of 50 weeks.

Systolic blood pressure decreased approximately 6 mmHg in the whole patient population from the start of treatment (week 0) both to week 38 (p=0.0001) and to week 50 (p=0.0002). There was no change in systolic blood pressure during the last 24 weeks of treatment. After 50 weeks of treatment the systolic blood pressure had decreased in all 4 treatment groups. There were no differences between the groups (p=0.88).

The diastolic blood pressure decreased approximately 2 mmHg after 38 weeks of treatment (p=0.02) and 4 mmHg after 50 weeks of treatment (p=0.0002) in the whole patient population. After 50 weeks of treatment, the diastolic blood pressure decreased in all 4 treatment groups, although not statistically significant in the EFK group (p=0.15). There were no significant differences between the groups (p=0.57).

At week 38 and 50, average heart rate decreased insignificantly for the whole patient population.

Laboratory Methods

For analysis of changes in the parameters, differences between week 50 and week 0 were used. There were no changes in laboratory values, except significantly decreased serum triglycerides, fasting glucose and cholesterol, (Table 12, 13 and 14, respectively).

TABLE 12

Mean difference in fasting serum glucose during the 50 weeks study

| Week | Treatment Group | | | | Total mean |
|---|---|---|---|---|---|
| | EFK | Ephedrine | Caffeine | Placebo | |
| 0[a] | 4.98 | 5.34 | 5.21 | 5.16 | 5.17 |
| 24[b] | −0.37 | −0.46 | −0.42 | −0.35 | — |
| 24 | (0.0001) | (0.002) | (0.0006) | (0.002) | — |
| 50[b] | −0.53 | −0.87 | −0.4 | −0.55 | −0.58 |
| 50 | (0.0003) | (0.003) | (0.001) | (0.0002) | (0.0001) |

[a] initial values are given (reference value 4.2–6.2 mmol/l)
[b] difference from initial values.

The numbers in parenthesis are significance values, p. Students one-sample t-test (SAS Univariate)

TABLE 13

Mean difference in fasting serum cholesterol

| Week | Treatment Group | | | | Total mean |
|---|---|---|---|---|---|
| | EFK | Ephedrine | Caffeine | Placebo | |
| 0[a] | 5.64 | 5.47 | 5.94 | 6.01 | 5.77 |
| 24[b] | −0.07 | −0.18 | −0.28 | −0.26 | — |
| 24 | (0.7) | (0.16) | (0.01) | (0.08) | — |
| 50[b] | −0.19 | −0.21 | −0.34 | −0.35 | −0.28 |
| 50 | (0.26) | (0.26) | (0.07) | (0.07) | (0.002) |

[a] initial values are given (reference value 3.5–8.0 mmol/l)
[b] difference from initial values.

The numbers in parenthesis are significance values, p. Students one-sample t-test (SAS Univariate).

TABLE 14

Mean difference in fasting serum triglycerides

| Week | Treatment Group | | | | Total mean |
|---|---|---|---|---|---|
| | EFK | Ephedrine | Caffeine | Placebo | |
| 0[a] | 1.68 | 1.56 | 1.51 | 1.95 | 1.67 |
| 24[b] | −0.57 | −0.66 | −0.32 | −0.86 | — |
| 24 | (0.001) | (0.004) | (0.002) | (0.01) | — |
| 50[b] | −0.85 | −0.67 | −0.45 | −1.40 | −0.83 |
| 50 | (0.0009) | (0.007) | (0.003) | (0.02) | (0.0001) |

[a] initial values are given (reference value 0.09–1.41 mmol/l
[b] difference from initial values.

The numbers in parenthesis are significance values, p. Students one-sample t-test (SAS Univariate).

Metabolic factors

Fasting glucose

As seen from Table 12, a large fall (more than 10%=0.58 mmol/l) was seen in the fasting serum glucose values. There were no differences between the groups.

Cholesterol

The treatment had effect on serum cholesterol after 50 weeks. As seen from Table 13, significant changes were found after 24 weeks (Example 5) but at week 50, serum cholesterol had fallen in all 4 groups. The fall was substantial (about 5%) and significant (p=0.002). There were no differences between the groups.

Triglycerides (TGA)

The treatment decreased the serum TGA. As seen from Table 14, the fall was substantial (about 20%) and highly significant (p=0.0001). There were no differences between the groups.

Apart from this, 2 patients had increased bilirubin values at the end of the study, but they had no other signs of liver affection.

In addition to the results from Example 5 the described open evaluation study has shown:

1. EFK is a safe and effective treatment of overweight or obesity when combined with a 5.04 MJ/day diet,
2. the obtained weight reduction after administration of EFK in weeks 0–24 is sustained during the study,
3. treatment with EFK results in a significant decrease in serum cholesterol, triglyceride and glucose concentrations.

EXAMPLE 7

Determination of isothermogenic efficiency of methylxanthines: Theophylline, caffeine and a combination Aim The objectives of the study are to examine the relation between the thermogenic effect of 3 selected doses of theophylline (50 mg, 100 mg and 200 mg), caffeine 200 mg, a combination of 30 mg caffeine and 50 mg theophylline, and placebo. A possible dose-response relation for the effect of theophylline will be studied, and the isothermogenic doses of caffeine and theophylline will be identified.

In this context, the isothermogenic dosages of two or more compounds are the doses which after oral administration in 14-h fasted subjects increase whole body energy expenditure to the same extent, the body energy expenditure being integrated over at least 3 hours above baseline.

Study Design

The study is designed as a placebo-controlled, double-blind trial. The order of the tests will be entirely randomized.

Subject Selection 6 healthy, normal weight subjects of both sexes are included after the informed consent is obtained.

Excluded are subjects with a habitual intake of caffeine of more than 1–2 daily cups of coffee (>100–200 mg of caffeine). The volunteers are not allowed to take any medicine during the study apart from the trial medication.

Treatment administered

A. Treatment with theophylline tablet containing 50 mg, 100 mg or 200 mg of theophylline, respectively.
B. Treatment with caffeine tablets containing 200 mg of caffeine.
C. Treatment with a tablet containing a combination of 30 mg caffeine and 50 mg theophylline.
D. Treatment with a placebo tablet without content of active drug.

All tablets are identical with regard to weight, appearance and taste.

The tablets are administered orally as single doses with 300 ml of tap water.

The study plan, the effect evaluation comprising measurement of energy expenditure and application of various laboratory methods, safety evaluation and statistical analysis are described in detail in Example 2 whereto reference is made.

Results

From the data obtained, a dose-response relation of the effect of theophylline will be examined and the isothermogenic effect of theophylline and caffeine can be identified. Furthermore, the thermogenic effect of a combination of theophylline 50 mg and caffeine 30 mg will be determined.

EXAMPLE 8

A prospective, randomized, double-blind multi-center study in general practice of the weight-reducing effect of ephedrine/caffeine combination tablets (EFK) versus Isomeride® tablets containing dexfenfluramine in the treatment of obese patients Aim The aim is to examine the weight reducing effect and safety of EFK (ephedrine hydrochloride 20 mg in combination with caffeine 200 mg, DAK) and Isomeride® (dexfenfluramine 15 mg, Servier) combined with an energy restrictive diet and a program of increased physical exercise during 15 weeks of treatment in general practice.

Study design

The study was designed as a double-blind, randomized, parallel study with two treatment groups (Isomeride group and EFK group, respectively).

All patients were treated with the trial medication and prescribed a 5.0 MJ/day diet for 15 weeks. In addition, the patients received instructions for a program of increased physical exercise.

Patient Selection

Included were 103 patients of both sex, 53 patients in the Isomeride group and 50 patients in the EFK group. Patients were recruited from their general practitioners. The patients were included from 10 centers. The main part of the patients were included from 3 centers (67 patients), the remaining 7 centers included 4-7 patients each.

Included were patients aged between 18 and 75 years with more than 20% and less than 80% overweight and who had given their informed consent.

Excluded were:
1) Patients treated with anorexica within the last 2 months,
2) patients suffering from gastrointestinal diseases causing impaired drug absorption,
3) pregnant or lactating women, or women who wished to become pregnant,
4) patients with malignant diseases within the previous 5 years (except carcinoma basocellulare),
5) patients who had surgical treatment for their obesity, apart from cosmetic surgery,
6) patients with drug abuse or suffering from alcoholism, previously or at present,
7) patients with serious endocrinological diseases as for instance type I diabetes (IDDM) or thyreoidea diseases, the diseases requiring therapeutical treatment,
8) patients who had been treated with monoamine oxidase inhibitors within 14 days before entering the trial,
9) patients treated with drugs known to promote overweight, for instance lithium, valproate, tricyclic antidepressants or neuroleptics,
10) patients who had had changes in oestrogenic treatment within the last 3 months prior to the trial,
11) patients who had lost more than 8 kg during the last 2 months,
12) patients with hypertension (diastolic blood pressure more than 115 mmHg) and/or in need of antihypertensive treatment with antihypertensives other than diuretics,
13) patients with heart diseases, such as arrhythmia, the WPW syndrome or uncompensated heart diseases,
14) patients suffering from glaucoma, previously or at present,
15) patients suffering from depressions, previously or at present, or receiving psychiatric treatment.

81 patients completed the study: 43 in the Isomeride group and 38 in the EFK group.

22 patients dropped out of the study; 10 in the Isomeride group and 12 in the EFK group. 8 of the dropouts were caused by adverse drug reactions; 6 in the EFK group and 2 in the Isomeride group. 5 patients were excluded from the effect assessments since 7-10 weeks had elapsed between two of the control visits. The remaining dropouts were caused by outer reasons (treatment failure, adverse drug reactions (ADR), complications, pregnancy, non-compliance, unwillingness).

Weight data were analysed for the 81 patients who completed the study, while other data were analysed for all patients at an individual control visit.

Treatment Administered

A. EFK combination tablets containing 20 mg of ephedrine hydrochloride and 200 mg caffeine made according to Example 1C.
B. Placebo tablets without active drug.
C. Isomeride® capsules containing 15 mg dexfenfluramine.
D. Placebo capsules without active drug.

The tablets and the capsules, respectively, were identical with regard to weight, appearance and taste.

Treatment groups:
I: 1 EFK tablet three times daily and 1 placebo capsule twice daily.
II: 1 Isomeride® capsule twice daily and 1 placebo tablet three times daily.

Dosage 1 tablet and 1 capsule in the morning, 1 tablet at lunch and 1 tablet and 1 capsule in the evening for 15 weeks.

During the study, no other treatment for overweight or obesity was allowed. Only treatment which did not interact with the study medication was allowed after consultation with the general practitioner. Compliance was checked by counting the returned capsules and tablets.

Study plan

Before entering the study, the patients were informed about the study and their initial clinical condition was examined in order to decide whether the patients could be included according to the trial criterions. The patients' voluntary informed consent to participate in the study was obtained.

The age, height, weight and sex of the patients were recorded along with concomitant medication, and the patients received diet and exercise instructions. In addition, a blood sample was taken to check the relevant clinical parameters.

In the first, the third and every third week, the body weight, blood pressure and heart rate of the patients were recorded at control visits and the patients received diet and exercise instructions.

At the first control visit at the latest (week 1), the results of the laboratory values from the blood samples were evaluated. In case of abnormal values, the physician decided if the patient should be excluded.

Blood samples were taken after 0 and 15 weeks of treatment.

By randomization the patients were assigned to the two treatment groups. The sex distribution in the two groups was not statistically different ($p=0.52$). The average age of the patients were 42 years, average height 167 cm, average weight 91 kg, and the average % overweight was 46%. The two groups were comparable with respect to height ($p=0.62$), weight ($p=0.37$) and % overweight ($p=0.56$). The patients of the Isomeride group were younger than the patients of the EFK group, the average of the patients of the Isomeride group and EFK group being 39 years and 46 years, respectively (p=0.003). The average initial systolic blood pressure was 132 mmHg in the Isomeride group and 139 mmHg in the EFK group (p=0.06). The average initial diastolic blood pressure was 85 mmHg in the Isomeride group and 89 mmHg in the EFK group (p=0.12). The average initial heart rate for the whole population was 75 BPM and there was no difference between the groups (p=0.81). The mean body mass index (BMI) for the patients at week 0 was 33 kg/m$^2$, and there was no difference between the groups (p=0.62).

Effect Evaluation

Body weight

The patients were weighed on a decimal scale at each control visit.

Blood Samples

The effect of the treatment on the serum of cholesterol (total and HDL) were evaluated based on the results from the analysis of the blood samples taken at week 0 and 15.

Safety Evaluation

Subjective Methods

Adverse reactions were recorded by the general practioners at each visit either by indirect questioning or by spontaneous reporting by the patient.

Objective Methods

General physical examination

Before entering the trial, the general practitioner carried out a general physical examination on all patients.

Blood pressure and heart rate measurements.

At each control visit the blood pressure and the heart rate of the patients were measured according to the methods described in Example 5.

Laboratory Methods

At week 0 and 15, blood samples were taken.

The following tests were carried out:

Haematology parameters: Haemoglobin, haematocrit, erythrocytes, leucocytes, thrombocytes.

Liver parameters: Bilirubin, alkaline phosphateses. lactate dehydrogenase (LDH), aspartate aminotransferase SGOT/ASAT.

Kidney parameters: Creatinine

Metabolic factors: cholesterol (total and HDL)

All clinical-chemical analyses were carried out at The Medical Laboratories, Copenhagen, Denmark. The analyses performed were done according to well-accepted routine methods.

Statistical methods

The primary efficacy factor was the weight loss after 15 weeks of treatment.

Secondary parameters were clinical-chemistry values ADR systolic and diastolic blood pressure, and heart rate.

Data were typical, so-called repeated measurement profiles, and were analysed both traditionally (ordinary t-test) and with a method described by Kenward (35). Briefly, the idea of this method is to describe the weight at a given time by means of the weight from one or two previous measurement periods. Deviations one way or the other were attributable to a possible treatment effect. The method thus describes the actual evolution of data. The advantage of this analysis is that the resulting tests are independent and more sensitive than the traditional t-tests.

The statistical analysis was made on the following transformation of weight data:

$$d_i = \log_{10}(\text{weight}/\text{weight}_0)$$

of which $d_i$ is the transformed variable at week i, $\log_{10}$ is the decimal logarithm, $\text{weight}_i$ is the weight at week i, and $\text{weight}_0$ is the weight at week 0.

This transformation was used because patients with a higher degree of overweight lost more than patients with a lower degree of overweight.

The determination of the so-called ante-structure in data shows a strong and only slightly descending correlation between weeks, and a rising variance throughout the weeks. These conditions make ordinary variance analyses extremely difficult.

In order to comply with this problem, a number of the most immediate previous measurements for a given person was used to predict the new measurement. The necessary number of previous measurements depend on the size of the ante-structure. An estimate of the size is achieved by regarding the inverse correlation matrix. The degree of the ante-structure appears from the number of secondary diagonals in the matrix, which have a reasonable size. In the present case, a reasonable size was estimated to be two, i.e. two previous measurements are necessary for the test. The measurements at week 1 and 3 were special, since there was either none or only one previous measurement at these times, respectively.

The tests for treatment effect are, however, still independent. The following types of data are regarded:

The logarithm of (weight in week$_i$/weight in week$_0$).

Systolic blood pressure in week$_i$—systolic blood pressure in week$_0$.

Diastolic blood pressure in week$_i$—diastolic blood pressure in week$_0$.

Heart rate in week$_i$—heart rate in week$_0$.

An ordinary t-test is carried out for treatment effect at each time of measurement, and a t-test for treatment effect where the ante-structure is utilised.

Method for cardiovascular data analysis

Systolic and diastolic blood pressure and heart rate were analysed as described above, i.e. with an ordinary t-test at all times, and an adjustable t-test. The ante-structure is assumed to be the same as the one for weight: two.

Method for ADR analysis

The number of ADRs per treatment and the number of patients with ADRs are analysed with a $X^2$-test. The analyses cover total incidence of ADRs, number of patients with and without ADRs per week, and ADRs in different organ systems.

Method for clinical-chemistry data analysis

The values at inclusion and at week 15 were analysed with a simple t-test (SAS PROC t-test). The difference between the value at week 15 and the value at week 0 were also tested with a simple t-test (SAS PROC univariate).

Method for demographic data analysis

Any differences between the treatment groups with regard to demographic data (i.e. values at the start of the study) were tested with a t-test (SAS PROC t-test). There was no analysis for normal distribution of the population.

Results

Weight loss

The reduction in body weight after 15 weeks of treatment was 92.0% of the initial body weight in the Isomeride group and 90.5% of the initial body weight in the EFK group. This reduction corresponds to 6.9 kg in the Isomeride group and 8.3 kg in the EFK group, respectively. The weight data for the patients are shown in Table 15.

TABLE 15

Weight data for patients with valid efficacy data (all patients)

| WEIGHT (kg) | TREATMENT | |
|---|---|---|
| | ISOMERIDE | EFK |
| WEEK 00 | | |
| N | 43 | 38 |
| MEAN | 90.39 | 90.87 |
| STD | 13.84 | 12.00 |
| WEEK 01 | | |
| N | 43 | 38 |
| MEAN | 88.88 | 88.69 |
| STD | 13.71 | 12.28 |
| WEEK 03 | | |
| N | 43 | 38 |
| MEAN | 87.14 | 87.56 |
| STD | 13.65 | 12.50 |
| WEEK 06 | | |
| N | 43 | 38 |
| MEAN | 85.79 | 86.07 |
| STD | 14.02 | 12.69 |
| WEEK 09 | | |
| N | 43 | 38 |
| MEAN | 84.80 | 84.73 |
| STD | 13.94 | 12.96 |
| WEEK 12 | | |
| N | 43 | 38 |
| MEAN | 83.80 | 83.43 |
| STD | 14.13 | 13.02 |
| WEEK 15 | | |
| N | 43 | 38 |
| MEAN | 83.46 | 82.53 |
| STD | 14.74 | 13.12 |

In Table 16 and 17 are shown the t-test sizes.

Generally a weight loss was seen after both treatments. Treatment with Isomeride had a significantly larger weight loss (p=0.013) than treatment with EFK after one week for the patients who accomplished all 15 weeks.

At week 3, treatment Isomeride had a significantly larger weight loss than EFK. The significance was largest for the patients who accomplished all 15 weeks (adj-t-test, p=0.018).

At week 15, which was the actual point of assessment for the whole treatment, there was also a non-significant tendency towards EFK being better than Isomeride (adj-t-test, p=0.12)

Weight loss in patients having of body mass index, BMI, $\geq 30$.

BMI is defined as:

$$BMI = \frac{body\ weight\ (kg)}{(height\ (m))^2}$$

To compare overweight between individuals, the index BMI can be used as a measure when the variation in the height of the individuals within a given population is small. The normal range of BMI is in the range of 20–25 kg/m$^2$, overweight of grade I corresponds to a BMI in the range of 25–29.9 kg/m$^2$, overweight of grade II corresponds to a BMI in the range of 30–40 kg/m$^2$ and, finally, extreme overweight corresponds to a BMI>40 kg/m$^2$. An overweight of 20% corresponds to a BMI of about 26.4 kg/m$^2$ for male and 25.8 kg/m$^2$ for female, respectively.

Analysis of the weight data resulting from patients classified as being obese or extreme obese, i.e. having a BMI $\geq 30$ kg/m$^2$ was performed.

59 patients in the trial had a BMI $\geq 30$ kg/m$^2$; 29 patients from the Isomeride group and 30 patients from the EFK group. After 15 weeks of treatment the average body weight in the Isomeride group was 92.6% of the initial value and 90.1% in the EFK group, respectively. These values correspond to an average weight loss of 7.0 kg in the Isomeride group and 9.0 kg in the

TABLE 16

T-test sizes for the logarithm of the relative weight for those who accomplished all 15 weeks. T-test is an ordinary t-test at any time, adj-t-test is calculated by means of an ante-structure. Figures in brackets give the p-value of the tests.

| week | 01 | 03 | 06 | 09 | 12 | 15 |
|---|---|---|---|---|---|---|
| Isomeride | 43 | 43 | 43 | 43 | 43 | 43 |
| EFK | 38 | 38 | 38 | 38 | 38 | 38 |
| t-test | 2.53 | 0.20 | 0.26 | 0.70 | 0.88 | 1.25 |
| | (0.0133) | (0.8452) | (0.7944) | (0.4843) | (0.3891) | (0.2163) |
| adj-t-test | 2.53 | −2.42 | 0.09 | 1.24 | 1.39 | 1.57 |
| | (0.0133) | (0.0176) | (0.9267) | (0.2203) | (0.1700) | (0.1201) |

TABLE 17

T-test sizes for the logarithm of the relative weight for all who participated at a given time. T-test is an ordinary t-test at any time, adj-t-test is calculated by means of the ante-structure. Figures in brackets give the p-value of the tests.

| week | 01 | 03 | 06 | 09 | 12 | 15 |
|---|---|---|---|---|---|---|
| Isomeride | 51 | 51 | 51 | 49 | 47 | 46 |
| EFK | 50 | 47 | 44 | 41 | 41 | 40 |
| t-test | 1.80 | 0.23 | 0.29 | 0.96 | 0.92 | 1.41 |
| | (0.0746) | (0.8175) | (0.7742) | (0.3403) | (0.3615) | (0.1623) |
| adj-t-test | 1.80 | −1.99 | 0.28 | 1.68 | 1.20 | 1.79 |
| | (0.0746) | (0.0489) | (0.7838) | (0.0963) | (0.2339) | (0.0780) |

EFK group, respectively. The weight reduction after treatment with EFK was significantly better after 15 weeks compared to treatment with Isomeride. (adj-t-test, p=0.032).

Safety evaluation 50 patients complained of ADRs: 43% from the Isomeride group and 54% from the EFK group.

Most patients complained of ADRs at week 1; 16 in the Isomeride group and 19 in the EFK group (p=0.48). At week 3, 14 patients in the Isomeride group and 7 in the EFK group complained of ADRs (p=0.13). During the rest of the study only few patients complained of ADRs and there was no difference between the treatments.

There is a difference in the ADR pattern of the two treatments. Patients treated with EFK more frequently complained of insomnia, nausea, tremor and agitation, whereas the patients treated with Isomeride complained of nausea, thirst, dizziness, fatigue and paraesthesia. More patients in the EFK group complained of agitating symptoms (p=0.001) and palpitations (p=0.04) than in the Isomeride group, whereas more patients in the Isomeride group complained of gastrointestinal symptoms (p=0.025).

Blood pressure

After 15 weeks of treatment, the systolic blood pressure was lowered with 10.6 mmHg (p=0.0001) in the EFK group and 7.8 mmHg (p=0.001) in the Isomeride group. No difference between the treatment groups was observed (p=0.41).

Laboratory methods

Total serum cholesterol decreased during the 15 weeks of treatment in both groups. The decrease was 0.64 mmol/l in the Isomeride group (p= 0.0001) and 0.36 mmol/l in the EFK group (p=0.006), respectively. No difference between the groups was observed (p=0.14).

Conclusion

Treatment with EFK is an effective and safe treatment of patients having 20–80% overweight. The patients treated with EFK reduced their initial body weight to 90.5% compared to 92.0% for patients treated with Isomeride (p=0.12). This corresponds to a weight loss of 8.3 kg in the EFK group and 6.9 kg in the Isomeride group. In a subgroup of the patients, i.e. patients having a BMI≧30 kg/m$^2$ (59 patients), the mean reduction of the initial body weight was 90.1% (9.0 kg) in the EFK group, and 92.6% (7.0 kg) in the Isomeride group, the difference between the two groups being highly significant (p=0.03). Thus, treatment of obesity with EFK tablets comprising a combination of 20 mg ephedrine hydrochloride and 200 mg caffeine is superior to a treatment with Isomeride capsules.

In addition, serum cholesterol decreased after 15 weeks of treatment.

EXAMPLE 9

A double-blind placebo controlled study of the effect of thermogenic stimulation with ephedrine/caffeine combination tablets on obese women treated with a low energy diet Aim The purpose of the present study is to determine the effect of 8 weeks of treatment with a thermogenic/anoretic tablet containing a combination of ephedrine and caffeine (20 mg ephedrine hydrochloride and 200 mg caffeine) on energy intake and 24 hours energy expenditure in 40 obese females randomized to either active treatment or placebo in a double-blind design. The influence, if any, of β-adrenergic stimulation on protein catabolism and body composition will also be studied. 24 hours energy expenditure will be measured in the respiration chambers before treatment, on the first day of treatment without diet, and after 8 weeks of treatment with an energy restrictive diet.

Patient Selection

Included are 40 women aged between 18 and 60 years with an overweight or obesity of more than 30% and less than 80%, according to the Metropolitan Life Insurance Table, 1983. Informed consent is obtained from all patients included.

Excluded are:
1) Patients with hypertension (diastolic blood pressure more than 130 mmHg,
2) pregnant or lactating women,
3) patients with psychoses, drug addiction, or alcohol abuse,
4) patients with insulin-demanding DM, mb. Addison, mb. Cushing, hypo- or hyperthyroidism or other endocrinological diseases,
5) patients who had had surgical treatment for their obesity,
6) patients receiving treatment with drugs known to influence energy balance,
7) patients who had changed oral contraceptives during the last 2 months,
8) patients who had lost more than 8 kg within the last 2 months,
9) patients with abnormal laboratory values.

Treatment Administered

A. Combination tablets containing 20 mg ephedrine hydrochloride and 200 mg caffeine made according to Example 1C.
B. Placebo tablets without active drug All tablets are identical with regard to appearance, taste and weight.

The tablets are administered orally 3 times daily with 400 ml of tap water. Concomitantly a 1000 kcal diet/day is prescribed according to the diet principle described by Quaade and Astrup (34).

Study Plan 20 patients are allocated to each treatment group (A and B), and receive a 40 kcal/kg lean body mass (LBM) diet at least 1 week before the first stay in the respiration chamber. During the 24 hours stay in the respiration chamber, the energy expenditure is measured by indirect calorimetry. The stay in the chamber follows a standardized program with intake of food, bicycling etc.

After the first stay in the respiration chamber, the treatment with EFK or placebo tablets is started. Two more stays in the respiration chamber are performed at the first day of treatment and 8 weeks later. Furthermore, the patients are weighed and blood pressure and heart rate are measured every week, and at week 2, 4, 6 and 8, blood samples are taken for further analysis.

The data obtained will be evaluated by using statistical methods, e.g. multi-factor analysis of variance and the results will be presented to show any obtained difference in energy expenditure from the two treatment groups.

EXAMPLE 10

A veterinary study on the effect of a composition comprising a combination of ephedrine and caffein incorporated in the diet on the body composition of meat and fat, respectively, after oral administration in pigs.

Study design

The study is designed as a parallel study with 5 treatment groups in a 5×5 factorial design.

Animals

The experiment will be conducted with six litters of five barrows (cross-bred Danish land race×Yorkshire) from 60 to 100 kg body weight.

Barrows are chosen as experimental animals over female (gills) or entire male pigs due to the fact that barrows contain more fat. Thus, an effect showing a reduction in fat accretion caused by EFK is supposed to be more pronounced and easy to determine.

Number of animals

The number of animals proposed are based on the following assumptions:
1. Variation in meat content=7% ($=\sigma$), and
2. The experiment must be able to detect a difference ($\delta$) of 5%.

With these assumptions, the number of animals per treatment group can be calculated as follows (40):

$$n=(Z_\alpha+Z_\beta)^2 \sigma_D/\delta^2$$

Because the experiment is carried out with litter males, the observations can be considered as paired (40).

$$\text{hence } \sigma_D = \sqrt{2 \times \sigma} = \sqrt{2 \times 7}$$

$$n = 10.5 \frac{(\sqrt{2 \times 7})^2}{5^2}$$

and $(Z_\alpha + Z_\beta)^2 = 10.5$ for $\alpha = 0.005$ and $\beta = 0.10$ $$n = 6 \text{ animals/group}$$

With 5 treatment groups, the number of animals equals 6×5=30.

In a two-way analysis of variance, the degree of freedom can be divided between the overall mean [1], litters [4], treatments [4] and error [IC].

Treatment administered level is chosen due to the assumption that if EFK promotes protein synthesis, i.e. an increase of the body content of meat, such an effect will probably not be elucidated when feeding the pig with a diet having the normal content of proteins for optimal growth.

TABLE 18

Composition and chemical composition of the dietary powder to which various amounts of EFK is added

| Composition | % w/w | Chemical composition | % of dry matter |
|---|---|---|---|
| Barley | 51 | Crude protein | 21.4 |
| Wheat | 20 | Fat | 5.0 |
| Sojbean | 24 | Crude fibre | 4.7 |
| Fat | 2 | | |
| Dicalciumphosphate | 1.7 | NFE | 62.7 |
| CaCO3 | 0.7 | Lysine | 1.07 |
| Salt | 0.4 | Methionin + cystine | 0.74 |
| Micro, - vitamin mixture | 0.2 | Threonine | 0.79 |

Treatment group

Within the six litters, the barrows will be allocated to 5 treatment groups consisting of increasing dietary levels of EFK.

I: Placebo—no content of ephedrine hydrochloride nor caffeine in the diet.
II: 14 mg ephedrine hydrochloride and 140 mg caffeine per kg feed (in the following, the notation 14/140 mg EFK is used corresponding to ephedrine hydrochloride/caffeine).
III: 28/280 mg EFK in the feed
IV: 56/560 mg EFK in the feed
V: 112/1120 mg EFK in the feed.

Assuming that a barrow weighing 80 kg consumes about 3 kg feed daily (36, 37), the dietary levels of EFK will correspond to 0/0, 0.5/5, 1.0/10, 2.0/20 and 4/40 mg EFK per kg live weight. At 60 kg live weight, the feed uptake is about 2.7 kg daily whereas at 100 kg live weight, the feed uptake is 3.5 kg (36, 37). This means that the dose expressed per kg live weight change a little during the experimental period. This is illustrated in Table 19. Expressed per kg lean body weight, this difference will be lower because fat accretion increases during this period (36, 37).

TABLE 19

Changes in dose of EFK per kg body weight during the study

| | Ingested daily amount (mg/kg body weight) | | | | | |
|---|---|---|---|---|---|---|
| Treatment group | ephedrine hydrochloride (A*) | caffeine | ephedrine hydrochloride (B*) | caffeine | ephedrine hydrochloride (C*) | caffeine |
| I | 0 | 0 | 0 | 0 | 0 | 0 |
| II | 0.63 | 6.3 | 0.53 | 5.3 | 0.49 | 4.9 |
| III | 1.26 | 12.6 | 1.05 | 10.5 | 0.98 | 9.8 |
| IV | 2.52 | 25.2 | 2.1 | 21.0 | 1.96 | 19.6 |
| V | 5.04 | 50.4 | 4.2 | 42.0 | 3.92 | 39.2 |

(A*) = 60 kg body weight; 2.7 kg calculated feed uptake per day
(B*) = 80 kg body weight; 3.0 kg calculated feed uptake per day
(C*) = 100 kg body weight; 3.5 kg calculated feed uptake per day All treatment groups (I, II, III, IV and V) will ingest the appropriate combination of ephedrine hydrochloride and caffeine via the diet in the form of a powder. The composition of the diet is shown in Table 18. Different amounts of ephedrine hydrochloride and caffeine is added to the dietary powder before use and intimately mixed in order to obtain the correct concentration of EFK in the dietary powder. The pigs are fed ad libitum throughout the study. The dietary level of proteins is higher than normal (17%) for optimal growth. A higher The selection of the dosage ranges is made based on the results from the human studies in which a dose of 20/200 mg EFK administered 3 times daily was effective, i.e. a dose corresponding to about 0.5–0.7 mg ephedrine hydrochloride and 1.5–2.3 mg caffeine, respectively, per kg body weight.

Furthermore, it is known that salbutamol in an amount of 3 ppm (3 mg/kg feed) decreases fat accretion and increases protein accretion in growing pigs (38, 39).

For human treatment of asthma, the recommended dose is ten times higher for ephedrine than for salbutamol. Thus, it is likely to assume that the optimal response of EFK on pigs will be within the proposed range.

Study plan

Registration during growth

Feed uptake and weight of the pigs will be registered weekly. From these data daily gain of weight, feed uptake and feed utilization will be calculated.

Slaughtering

At 100 kg body weight the pigs will be stunned in an atmosphere of carbondioxid and bled. The carcasses will be dissected into meat, subcutaneous fat, intermuscular fat, skin and bones. Furthermore, the cross-sectional area of M. longissimus dorsi at the last rib will be measured (53). The dissection procedure allows for a calculation of the different anatomic dissected fractions in relation to the weight of the carcass, and to determination of the fat tissue mass/lean mass body mass ratio.

The data obtained will be evaluated using statistical methods, e.g. a multi-factor analysis of variance and the results will be presented to show any obtained difference in the body content of meat and fat, respectively, from the 5 treatment groups.

REFERENCES

1. Council on Scientific Affairs (1988). Treatment of obesity in adults. *JAMA* 260, 2547–48.
2. Dulloo, A. and D. S. Miller (1989). Ephedrine, caffeine and aspirin: "Over-the-counter" drugs that interact to stimulate thermogenesis in the obese. *Nutrition* 5, 7–9.
3. Astrup, A. V. (1989). Treatment of obesity with thermogenic agents. *Nutrition* 5, p. 70.
4. Astrup A. (1986). Thermogenesis in human brown adipose tissue and skeletal muscle induced by sympatomimetic stimulation. *Acta Endocrinol.* 112, suppl. 278, 1–32.
5. Hollands, M. A., J. R. S. Arch and M. A. Cowthorne (1981). A simple apparatus for comparative measurements of energy expenditure in human subjects: The thermic effect of caffeine. *Am.J.Clin.-Nutr.* 34, 2291–2294.
6. Astrup, A., J. Bülow, J. Madsen and N. J. Christensen (1985). Contribution of BAT and skeletal muscle to thermogenesis induced by ephedrine in man. *Am.J.Physiol.* 248, E 507–514.
7. Astrup, A. (1987) Reduced energy expenditure contributes to obesity in predisposed individuals: Implications for treatment with thermogenic agents. *J.Obes.Weight Reg.* 6, 3–20.
8. Dulloo, A. G. and D. S. Miller (1986). The thermogenic properties of ephedrine/methylxanthine mixtures: Human studies. *Int.J.Obesity* 10, 467–481.
9. Cesari, H. P., R. Pasquali, F. Casimirri, N. Melchionda, C. Stefanini and A. Raitano (1989). The therapeutic dilemma of ephedrine in obesity and the inefficacy of caffeine. *Int.J.Obesity* 13, Suppl. 1, 152.
10. Eriksen, N. (1982). U.K. Patent 2004183B.
11. Editorial (1984). Drug Treatment, July 1984, 43–51.
12. Sebok, M. (1985). A double-blinded placebo-controlled, clinical study of the efficacy of a phenylpropanolamine/caffeine combination product as an aid to weight loss in adults. *Curr.Ther.Res.* 37, 701–708.
13. Goth, A. (1981). Medical Pharmacology, 10th. Ed., Mosby Publ., U.S.A. p. 190ff.
14. Arch, J. R. S., A. T. Ainsworth, M. A. Cawthorne, V. Piercy, M. V. Sennitt, V. E. Thody, C. Wilson and S. Wilson (1984). *Nature,* 309, 163–165.
15. Reminton's Pharmaceutical Sciences, 16th. Ed. (1980), Mack Publishing Company, Easton, U.S.A.
16. Durnin, J. V. G. A. and J. Womersley (1974). Body fat assessed from total body density and its estimation from skinfold thickness. *Br.J.Nutr.* 32, 77–97.
17. Jecquier, E. (1987). Energy metabolism in the human body. In Bender, A. E. and L. J. Brookes (eds.): Body weight control, Churchill Livingstone, 17.
18. Segal, K. R. (1987). Comparison of indirect calorimetric measurements of resting energy expenditure with a ventilated hood facemask, and mouth piece. *Am.J.Clin.Nutr.* 45, 1420–1423.
19. Scholander, P. F. (1947). Analyses for accurate estimation of respiratory gases in one-half cubic centimeter samples. *J.Biol.Chem.* 167, 235.
20. Weir, J. B. de V. (1949). New methods for calculating metabolic rate with special reference to protein metabolism. *J. Physiol.* 109, 1–9.
21. Garby, L. and A. Astrup (1987). The relationship between the respiratory quotient and the energy equivalent of oxygen during simultaneous glucose and lipid oxidation and lipogenesis. *Acta Physiol.Scand.* 129, 443–444.
22. Laurell, S. and G. Tibbling (1967). Colorimetric microdetermination of free fatty acids in plasma, *Clin.Chim.Acta,* 16, 57–62.
23. Bergmayer, H. V. and E. Bernt. Bestimmung mir Glucoseoxydase und Peroxydase (1970). In Bergmayer H. V. (ed.): Methoden der enzymatischen Analyse, Verlag Chemie, Wenheim, 1172–1181.
24. Laurell, S. and G. Tibbling (1966). An enzymatic fluorometric micromethod for the determination of glycerol. *Clin.Chem.Acta* 13,317–322.
25. Noll, F. (1974) L(+)-Lactate. Determination with LDH, GPT and NAD. In Bergmeyer H V. (ed.): Methods of enzymatic analysis, 2nd ed., Academic Press, New York, 1475.
26. Giegel, J. L., A. B. Ham and W. Clema (1975). Manual and semiautomated procedures for measurement of triglyceride in serum. *Clin.Chem.* 21, 1575–1581.
27. Christensen, N. J., P. Vestergaard, T. Sorensen and O. J. Rafealsen (1980). Cerebrospinal fluid adrenaline and noradrenaline in depressed patients. *Acta Psychiat.Scand.* 61, 178–182.
28. Brown, B. W. and M. Hollander (1977). Statistics, a biochemical introduction, John Wiley & Son, New York, 261–292.
29. Willems, H. J. J., A. van der Horst, P. N. F. C. de Goede and G. J. Haakmeester (1985). Determination of some anticonvulsants, antiarrhytmics, benzodiazepines, xanthines, paracetamol and chloramphenicol by reversed phase HPLC. *Pharm.Weekbl.Sci.Ed.* 7, 150.
30. Lurie, I. S. (1981). Improved isocratic mobile phases for the reverse phase ion-pair chromatographic analysis of drugs of forensic interest. *J.Liq.Chromatogr.* 4, 339.
31. Lai, C. M., R. G. Stoll, Z. M. Look and A. Jacobi (1979). Urinary excretion of chlorpheniramine and pseudoephedrine in humans. *J.Pharm.Sci.* 68, 1243.

32. Nelder, J. A. and R. Mead (1965). *Comput.J.* 7, 308.
33. Andersen, T., O. G. Backer, A. Astrup and F. Quaade (1986). *Nutrition* 2, 83–86.
34. Quaade, F. and A. Astrup (1988). Is a good quality of life compatible with a slimming diet? What can we do to make dieting easier for the obese. *Medicographica* 10, 21–23.
35. Kenward, M. G. (1987). A method for comparing profiles of repeated measurements. *Appl. Statist.* 36, 296–308.
36. Whitlemore, C. T., Tullis, J. B. & Emmans, G. S. 1988. Protein growth in pigs. *Anim. Prod.* 46, 437–445.
37. Donker, R. A., Den Harlog, L. A., Brascamp, E. W., Merks, J. W. M., Noordewier, G. J. & Buiting, G. A. J. 1986. Restriction of feed intake to optimize the overall performance and composition of pigs. *Livest. Prod. Sci.* 15, 353–365.
38. Oksbjerg, N., Blackshaw, A., Henckel, P., Fernandez, J. A. F. & Agengaard, N. 1990. Alterations in protein accretion and histochemical characteristics of the M. longissimus dorsi in pigs caused by salbutamol (a $\beta$-adrenergic agonist). *Acta Agric. Scand.* (submitted).
39. Warriss, P. D., Kerstin, S. C., Rolph, T. P. & Brown, S. N. 1990. The effects of the beta-adrenergic agonist salbutamol on meat quality in pigs. *J. Anim. Sci.* 68, 128–136.
40. Snedecor, G. W. & Cockran, W. G. Statistical Methods. Sixth edition. Ames, Iowa, USA.
41. Jensen, K. B., Dano, P. Draeby, N., Hansen, S. H. & Kanstrup, J. 1980, Helsinger-pillen som slankemiddel. *Ugeskr. Laeger,* 1499–1501.
42. Williams, P. E. V. 1987. The use of $\beta$ agonists as a means of altering body composition in livestock species. *Nutrition Abstracts and Reviews* (Series B). 57, 453–464.
43. Hanrahan, J. P. 1987. Beta-agonists and their effects on animal growth and carcass quality. *Elsevier Applied Science,* London and New York.
44. Anderson, D. B., Veenhuizen, E. L., Waitt, W. P. Paxton, R. E. and Young, s.s. 1987. The effect of dietary protein on nitrogen metabolism, growth performance and carcass composition of finishing pigs fed ractopamine. *Federation Proceedings.* 1021 (Abstract).
45. Warris, P. D. Kestin, S. C., Rolph, T. P. and Brown, S. N. 1990. The effects of the beta-adrenergic agonist salbutamol on meat quality in pigs. *J. Anim. Sci.* 68, 128–136.
46. Buttery, P. J. and Dawson, J. H. 1987. The mode of action of beta-agonists as manipulators of carcass composition. In "Beta-agonists and their effects on animal growth and carcass quality". *Elsevier Applied Science,* London and New York, 29–44.
47. Veenhuizen, E. L. Schmiegel, K. K., Waitt, W. P. and Anderseon, D. B. 1987, Lipolytic growth, feed efficiency, and carcass responses to phenethanolamines in swine. *J. Anim. Sci.* 65, 130.
48. Peterla, T. A., Richs, C. A. and Scanes, C. G. 1987. Comparison of effects of $\beta$ agonists and recombinant bovine somatotropin on lipolysis and lipogenesis in ovine adipose tissue. *J. Anim. Sci.* 65, 278.
49. Peterla, T. A., Richs, C. A. and Scanes, C. G. 1988. Cimaterol, $\alpha$-, $\beta$-adernergic agonist, directly affects lipolysis and lipogenesis in porcine adipose tissue in vitro. *J. Anim. Sci.* 66, 249.
50. Thornton, R. F., Tume, R. K., Payne, G., Larsen, T. W., Johnson, G. W., and Hohenhaus, M. A., 1985. The influence of the $\beta_2$-adrenergic agonist, clenbuterol, on lipid metabolism and carcass composition of sheep. *Proc. New Zealand Soc. Anim. Prod.* 45, 97–101.
51. Adeola, O., Ball, A. O., Young, L. G., 1989, Ractopamine stimulates porcine myofibrillar protein synthesis, *J. Anim. Sci.* 67, Suppl. 1, 191.
52. Wilson, M. A. Zhong, C., Forsberg, N. E., Dalrymple, R. H. and Ricks, C. A. 1988. Effects of cimaterol on protein synthesis protein degradation, amino acid transport and acetate oxidation in sheep external infercostal muscle. *Nutrition Research* 8, 1287–1296.
53. EEC 1979. Development of uniform methods for pig carcass classification in the EEC Document VI/5804/78 rev.

I claim:

1. A method for reducing the weight of a human, comprising:
   administering to the human a thermogenically effective dose of an ephedrine and caffeine in a weight ratio of about 1:12, calculated on the amount of ephedrine in the form of the free base, said dose being administered either as a single dose comprising a combination of ephedrine and caffeine or as separate doses administered substantially concomitantly and each dose containing one of ephedrine and caffeine, respectively.

2. A method according to claim 1, wherein the ephedrine is at least one of a L-ephedrine selected from the group consisting of (1R, 2S)-2-methyl-amino-1-phenyl-1-propanol or a pharmaceutically acceptable salt thereof and (1S, 2R)-2-methylamino-1-phenyl-1-propanol or a pharmaceutically acceptable salt thereof.

3. A method according to claim 1, wherein the caffeine is in the form of a pharmaceutically acceptable salt or a complex thereof.

4. A method according to claim 1, wherein the amount of the ephedrine is about 10–40 mg per unit dose, calculated on the amount of ephedrine in the form of the free base.

5. A method according to claim 1, wherein the amount of the ephedrine is about 16–17 mg per unit dose, calculated on the amount of ephedrine in the form of the free base.

6. A method for reducing the adipose tissue mass/lean mass body mass ratio of a human, comprising:
   administering to the human a thermogenically effective dose of an ephedrine and caffeine in a weight ratio of about 1:12, calculated on the amount of ephedrine in the form of the free base, said dose being administered either as a single dose comprising a combination of ephedrine and caffeine or as separate doses administered substantially concomitantly and each dose containing one of ephedrine and caffeine, respectively.

7. A method according to claim 6, wherein the ephedrine is at least one of a L-ephedrine selected from the group consisting of (1R, 2S)-2-methyl-amino-1-phenyl-1-propanol or a pharmaceutically acceptable salt thereof and (1S, 2R)-2-methylamino-1-phenyl-1-propanol or a pharmaceutically acceptable salt thereof.

8. A method according to claim 6, wherein the caffeine is in the form of a pharmaceutically acceptable salt or a complex thereof.

9. A method according to claim 6, wherein the amount of the ephedrine is about 10–40 mg per unit dose, calculated on the amount of ephedrine in the form of the free base.

10. A method according to claim 6, wherein the amount of the ephedrine is about 16–17 mg per unit dose, calculated on the amount of ephedrine in the form of the free base.

11. A method for reducing the fat tissue mass/lean mass body mass ratio of a domestic animal, comprising:
   administering to the animal an effective dose of a combination of an ephedrine and caffeine in a weight ratio of about 1:12, calculated on the amount of ephedrine in the form of the free base.

12. A method according to claim 11, wherein the ephedrine is at least one of a L-ephedrine selected from the group consisting of (1R, 2S)-2-methyl-amino-1-phenyl-1-propanol or a pharmaceutically acceptable salt thereof and (1S, 2R)-2-methylamino-1-phenyl-1-propanol or a pharmaceutically acceptable salt thereof.

13. A method according to claim 11, wherein the caffeine is in the form of a pharmaceutically acceptable salt or a complex thereof.

14. A method according to claim 11, wherein the domestic animal is selected from the group consisting of cattle, pigs and sheep.

* * * * *